(12) United States Patent
Korchia-Maor

(10) Patent No.: US 11,160,750 B2
(45) Date of Patent: Nov. 2, 2021

(54) COMPOSITION AND METHOD FOR PROMOTING HAIR GROWTH

(71) Applicant: ZivMas LLC, Teaneck, NJ (US)

(72) Inventor: Yehoshua Korchia-Maor, Jerusalem (IL)

(73) Assignee: ZIVMAS LLC, Teaneck, NJ (US)

( * ) Notice: Subject to any disclaimer, the term of this patent is extended or adjusted under 35 U.S.C. 154(b) by 0 days.

(21) Appl. No.: 16/635,602

(22) PCT Filed: Aug. 2, 2018

(86) PCT No.: PCT/US2018/044935
§ 371 (c)(1),
(2) Date: Jan. 31, 2020

(87) PCT Pub. No.: WO2019/028214
PCT Pub. Date: Feb. 7, 2019

(65) Prior Publication Data
US 2020/0237642 A1 Jul. 30, 2020

Related U.S. Application Data

(60) Provisional application No. 62/540,591, filed on Aug. 3, 2017.

(51) Int. Cl.
| | |
|---|---|
| A61K 8/9789 | (2017.01) |
| A61K 8/9794 | (2017.01) |
| A61K 8/27 | (2006.01) |
| A61K 8/34 | (2006.01) |
| A61K 8/365 | (2006.01) |
| A61K 8/67 | (2006.01) |
| A61K 8/44 | (2006.01) |
| A61K 8/73 | (2006.01) |
| A61K 8/60 | (2006.01) |
| A61Q 7/00 | (2006.01) |
| A23L 33/175 | (2016.01) |
| A23L 33/155 | (2016.01) |
| A23L 33/105 | (2016.01) |

(52) U.S. Cl.
CPC .......... A61K 8/9789 (2017.08); A23L 33/105 (2016.08); A23L 33/155 (2016.08); A23L 33/175 (2016.08); A61K 8/27 (2013.01); A61K 8/34 (2013.01); A61K 8/365 (2013.01); A61K 8/44 (2013.01); A61K 8/602 (2013.01); A61K 8/673 (2013.01); A61K 8/731 (2013.01); A61K 8/732 (2013.01); A61K 8/9794 (2017.08); A61Q 7/00 (2013.01)

(58) Field of Classification Search
CPC combination set(s) only.
See application file for complete search history.

(56) References Cited

U.S. PATENT DOCUMENTS

| | | | | |
|---|---|---|---|---|
| 5,486,509 A | * | 1/1996 | Jimenez | A61K 38/1808 514/167 |
| 6,149,933 A | * | 11/2000 | Nelson | A61K 8/673 424/441 |
| 6,207,203 B1 | * | 3/2001 | Atkinson | A23F 5/40 426/594 |
| 2015/0209399 A1 | * | 7/2015 | Fields | A61K 31/216 424/769 |
| 2015/0328101 A1 | | 11/2015 | Trigiante | |
| 2016/0296440 A1 | * | 10/2016 | Shin | A61Q 19/08 |

FOREIGN PATENT DOCUMENTS

| | | | | |
|---|---|---|---|---|
| WO | WO-9423689 A1 * | 10/1994 | | A61K 36/81 |
| WO | WO-2007000214 A1 * | 1/2007 | | A61Q 19/00 |
| WO | WO-2008073684 A1 * | 6/2008 | | A61P 17/16 |
| WO | WO2008073684 A1 | 6/2008 | | |
| WO | WO-2011103449 A2 * | 8/2011 | | A61K 36/185 |
| WO | WO2011103449 A2 | 8/2011 | | |
| WO | WO-2014010900 A1 * | 1/2014 | | A61P 17/14 |
| WO | WO-2015118281 A1 * | 8/2015 | | A61K 8/9789 |
| WO | WO-2016057839 A1 * | 4/2016 | | A61K 9/145 |
| WO | WO2016057839 A1 | 4/2016 | | |
| WO | WO-2016199147 A1 * | 12/2016 | | A61K 8/9783 |
| WO | WO2016199147 A1 | 12/2016 | | |

OTHER PUBLICATIONS

A. Gordon, et al. Chemical characterization and evaluation of antioxidant properties of Açaí fruits (*Euterpe oleraceae Mart.*) during ripening Food Chemistry 133 (2012) 256-263. (Year: 2012).*
H. Jemai, A. El Feki, S. Sayadi. Antidiabetic and Antioxidant Effects of Hydroxytyrosol and Oleuropein from Olive Leaves in Alloxan-Diabetic Rats. J. Agric. Food Chem. 2009, 57, 8798-8804. (Year: 2009).*
Google Patent Search, Jul. 23, 2020 (Year: 2020).*
Google Scholar Search, Nov. 7, 2020 (Year: 2020).*
Google Search, Nov. 1, 2020 (Year: 2020).*
"Douglas Laboratories 2016 Best Sellers: Pushing Potential," cited by the Applicant in the IDS dated Mar. 17, 2020 (Year: 2016).*
Machado, et al. Neuroprotective Effects of Acai (*Euterpe oleracea Mart.*) Against Rotenone In Vitro Exposure, "Oxidative Medicine and Cellular Longevity,"2016, 1-14 (Year: 2016).*
Machine translation WO2015118281A1 (Year: 2020).*
Machine translation WO2007000214A1 (Year: 2020).*
F. R. Garcez, W. S. Garcez, T. S. Mahmoud, P. de Oliveira Figueiredo. New Constituents From the Trunk Bark of Tabebuia heptaphylla. Quim. Nova, vol. 30, No. 8, 1887-1891, 2007. (Year: 2007).*

(Continued)

Primary Examiner — Michael P Cohen
(74) Attorney, Agent, or Firm — Greer, Burns & Crain, Ltd.

(57) ABSTRACT

Compositions comprising one or more of the following extracts: an *Euterpe oleracea* extract comprising cyanidin 3-glycoside and/or cyanidin 3-rutinoside, an *Olea europaea* extract comprising oleuropein, a *Coffea arabica* extract, and/or a *Tabebuia impetiginosa* extract. The compositions further comprise a micronutrient comprising zinc and vitamin D3. Dietary supplements and hair/body care products comprising the compositions. The compositions are useful for non-medicinal treatment of hair loss and/or nourishment and rejuvenation of hair, skin and nails.

17 Claims, 15 Drawing Sheets

(56) References Cited

OTHER PUBLICATIONS

Simone Digital ("Know Your Beauty Ingredients: Açaí Berry," downloaded Mar. 15, 2021 from http://simonedigital.com/acai-berry-for-hair-growth/. available Oct. 12, 2014 (Year: 2014).*

English translation WO 94/23689 A1 (Year: 2021).*

Jordan M. Thompson, Mehwish A. Mirza, Min Kyung Park. The Role of Micronutrients in Alopecia Areata: A Review Am J Clin Dermatol (2017) 18: 663-679. (Year: 2017).*

Chemist Direct. "Pantoten & Hair Growth," accessed online Mar. 16, 2021 at https://web.archive.org/web/ 20140612080951/https://www.chemistdirect.co.uk/bioconcepts-h-pantoten-and-hair-growth, dated Jun. 14, 2014. (Year: 2014).*

Oral Oleuropein for baldness—Google Scholar search—Mar. 13, 2021 (Year: 2021).*

Pantothenate for hair loss—Google Search—Mar. 16, 2021 (Year: 2021).*

Douglas Laboratories, "Douglas Laboratories 2016 Best Sellers: Pushing Potential", 2016, p. 3, left col., Section 2.3; p. 4, left col.; p. 10, left col., p. 12, left col., to p. 12, right col.; p. 21, right col.

Machado, A., et al., "Neuroprotective Effects of Acai (*Euterpe oleracea Mart.*) against Rotenone In Vitro Exposure" Hindawi Publishing Corp., Oxidative Medicine and Cellular Longevity, pp. 1-15, vol. 2016.

Tong, T. et al., "Topical Application of Oleuropein Induces Anagen Hair Growth in Telogen Mouse Skin", Plos One, Jun. 10, 2015, pp. 1-17, vol. 10, No. 6.

Nikitha, "Benefits/Uses of Green Coffee Beans for Skin, Hair and Health", Stylish Walks, Jul. 2015, pp. 1-7.

* cited by examiner

CTL

2mg/ml ZM-26 capsule + 5μM testosterone

5μM testosterone

2mg/ml ZM-26 liquid + 5μM testosterone

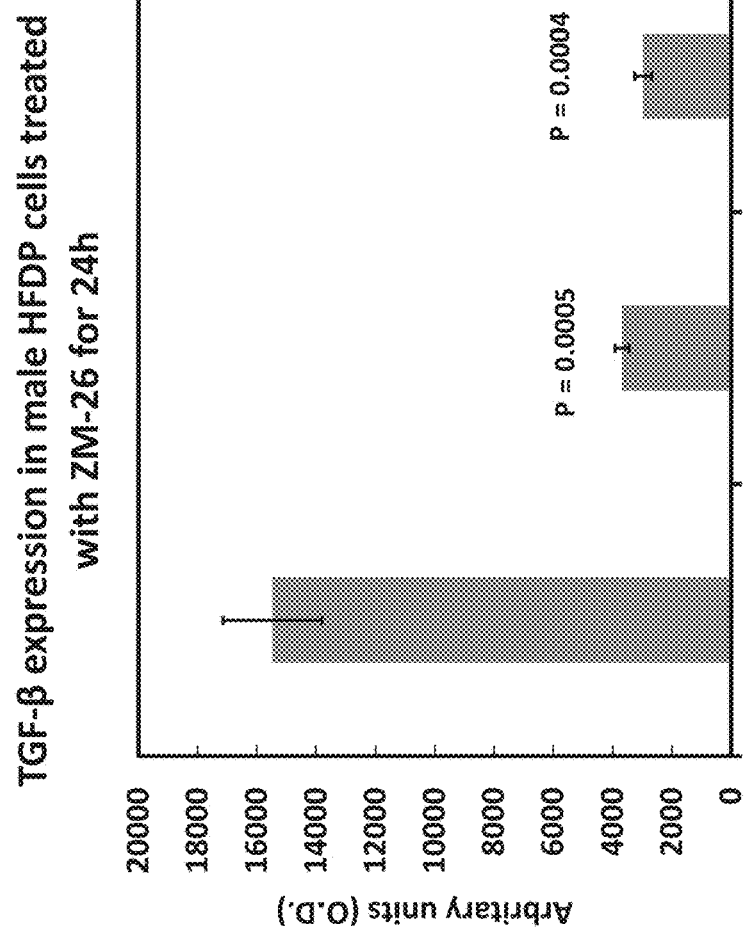
Fig. 18A
Fig. 18B

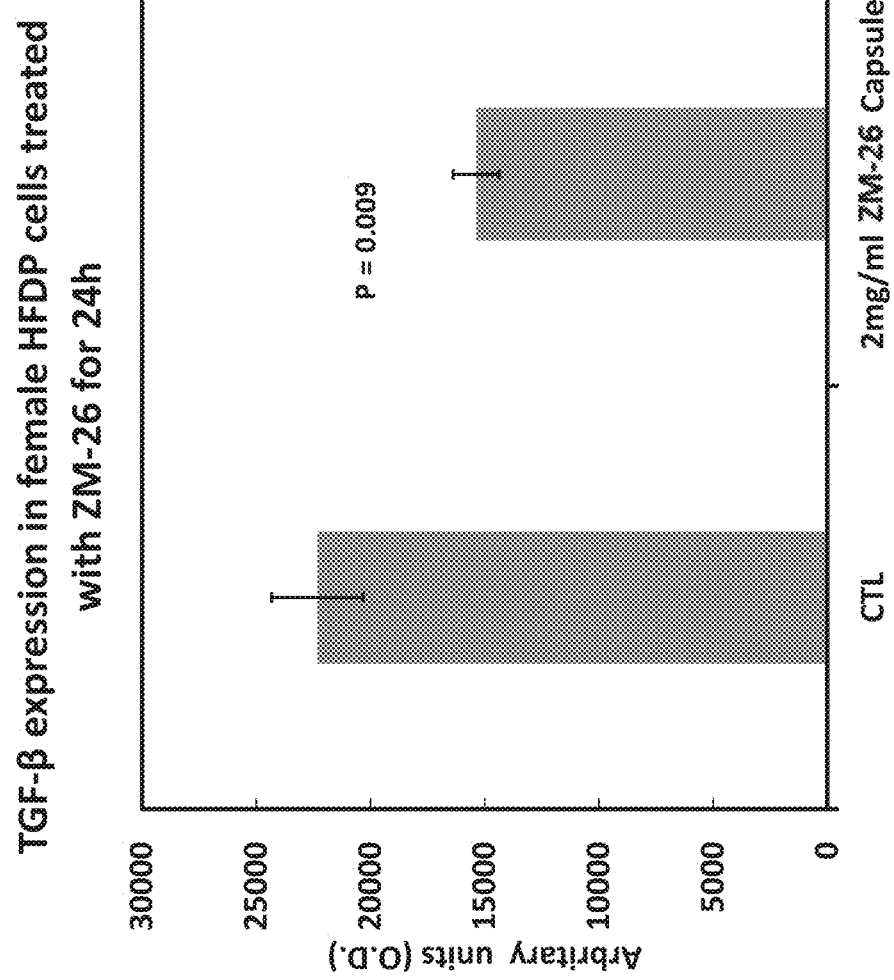

COMPOSITION AND METHOD FOR PROMOTING HAIR GROWTH

CROSS-REFERENCE TO RELATED APPLICATIONS

This application is the U.S. National phase application corresponding to PCT/US2018/044935 which was assigned an international filing date of Aug. 2, 2018 and associated with publication WO 2019/028214 A1 and which claims priority to U.S. Provisional Application No. 62/540,591 filed on Aug. 3, 2017, the disclosures of which are expressly incorporated herein by reference.

TECHNICAL FIELD

The present invention relates to compositions useful as dietary supplements and hair care and body care products. It also relates to methods with the compositions and uses for the compositions in restoring and rejuvenating hair, skin and nails.

BACKGROUND

Hair is a unique structure of the skin. A hair follicle (HF) is subject to constant turnover in the course of perpetual cycles through various stages of proliferation (anagen), involution (catagen), and resting (telogen)(1). The cycling and regeneration of each HF depends on specialized hair follicle dermal papilla cells (HFDPCs) and proliferating matrix cells located at the base of the hair follicle.

The HF cycling and regeneration are tightly controlled by several growth factors (2). Androgens, such as for example, testosterone and dihydrotestosterone, are also known to control hair growth. The androgens can trigger hair loss by stimulating expression of transforming growth factor-$\beta1$ (TGF-$\beta1$) in dermal papilla cells (DPCs), which leads to inhibition of epithelial cell growth (3). Another group of cells essential for hair maintenance are keratinocytes which reside mostly in the bulge region of the hair follicle and play a critical role in hair follicle regeneration (4).

Many diseases and maladies in the world are attributed to the effect of free radicals in the bloodstream and tissues of the human body. Among the problems attributed to free radicals are loss of hair, weakening of nails, and poor skin appearance. It would be useful to provide an effective and simple method for protecting the tissues of the body against free radicals and chronic inflammatory processes.

Hair loss affects both men and women, although the incidence rate in women is lower than in men. Many forms of alopecia are common in the general population and some patients may display more than one form of hair loss (21). Typically, there is also a difference in the balding patterns between men and women (1, 5).

Drug therapy and human hair transplantation are two methods available for treating androgenic alopecia (AGA). For hair transplantation, limitations include a restricted supply of transplantable hair and the cost of treatment (15). Approved drugs for hair loss include topical minoxidil and oral finasteride. Minoxidil promotes hair growth through increasing the duration of anagen by opening potassium channels in the cell membrane and expanding blood vessels of scalp (9). Unfortunately, the effect of minoxidil is temporary (10). Most common adverse reactions of the topical formulation are irritant and allergic contact dermatitis on the scalp, but a non-arteritic anterior ischemic optic neuropathy has been also reported in some patients (11).

Finasteride is a competitive inhibitor of 5α-reductase (type II)(12) approved for treatment of hair loss. However, finasteride has been associated with some sexual dysfunction such as ejaculation and libido disorders and erection dysfunction (13), and also may cause malformation of the external genitalia in male fetuses (14). Several natural substances have been discovered which may influence the expression of hair growth factors (16-18). Some plants produce anti-hair loss effects by inhibiting 5a-reductase (19).

Thus, there remains a need for new drugs and therapies which would prevent hair loss and enhance hair growth without significant side effects.

SUMMARY

The present disclosure helps with addressing at least some of these and other needs and provides compositions, dietary supplements and hair care and body care products which may help in rejuvenating hair, skin and/or nails and/or in promoting hair growth and/or help with hair maintenance.

In one aspect, this disclosure provides a composition comprising:
1) One or more of the following extracts:
   a) an *Euterpe oleracea* extract comprising cyanidin 3-glycoside and/or cyanidin 3-rutinoside,
   b) an *Olea europaea* extract comprising oleuropein,
   c) a *Coffea arabica* extract, and/or
   d) a *Tabebuia impetiginosa* extract;
2) a micronutrient comprising zinc; and
3) vitamin D3.

The composition may further comprise p-coumaric acid. In some of the compositions, p-coumaric acid is used in an amount from 0.2% to 3% by weight of the total weight of the composition. In some of the compositions, the micronutrient comprising zinc is used in an amount from 0.2% to 5% by weight of the total weight of the composition.

Some preferred compositions comprise the *Euterpe oleracea* berries extract; the *Olea europaea* leaves extract and the *Coffea arabica* green beans extract and they do not comprise the *Tabebuia impetiginosa* extract. Other preferred compositions comprise four extracts: the *Euterpe oleracea* berries extract; the *Olea europaea* leaves extract, the *Coffea arabica* green beans extract and the *Tabebuia impetiginosa* bark extract.

In the compositions provided in this disclosure, extracts may be used in the following ratios: about 100 parts of the *Euterpe oleracea* extract by volume; about 3 to 10 parts the *Olea europaea* extract by volume, about 3 to 10 parts of the *Coffea arabica* green beans extract by volume and about 0 to 4 parts of the *Tabebuia impetiginosa* extract. In some compositions of this disclosure, the *Euterpe oleracea* extract is 2:1 to 10:1 concentrate.

In the compositions of this disclosure, the extracts are preferably hydroalcoholic extracts. One preferred *Euterpe oleracea* extract is obtained from Acai berries. One preferred *Olea europaea* extract is obtained from *Olea europaea* leaves. One preferred *Coffea arabica* extract is obtained from *Coffea arabica* unroasted green beans.

The compositions of this disclosure downregulate expression of TGF-$\beta1$ protein. The compositions of this disclosure stimulate proliferation of hair follicle dermal papilla cells.

In the compositions of this disclosure the micronutrient comprising zinc may comprise zinc oxide or zinc picolinate.

Some compositions of this disclosure comprise a compound selected from the group consisting of: L-arginine, magnesium citrate, calcium d-pantothenate, and any combination thereof.

Some compositions of this disclosure comprise the *Euterpe oleracea* extract comprising cyanidin 3-glucoside and cyanidin 3-rutinoside; the *Tabebuia impetiginosa* extract; the *Olea europaea* dried leaves extract comprising oleuropein; the *Coffea arabica* (green coffee beans) extract, Vitamin D3; calcium d-pantothenate; magnesium citrate; and zinc picolinate.

Certain compositions in this disclosure can be formulated as follows: per each 100 to 150 mg of the *Euterpe oleracea* extract in a composition, the composition also comprises 55 to 105 mg of the *Tabebuia impetiginosa* extract, 55 to 105 mg of the *Olea europaea* dried leaves extract comprising oleuropein; 50 to 100 mg of the *Coffea arabica* (green coffee beans) extract, 200 to 2000 International Units (IUs) of Vitamin D3; 0 to 10 mg of calcium d-pantothenate; 0 to 100 mg of magnesium citrate; and 5 to 20 mg of zinc picolinate.

Some compositions of this disclosure comprise the *Euterpe oleracea* berries hydroalcoholic extract comprising cyanidin 3-glucoside and cyanidin 3-rutinoside; the *Tabebuia impetiginosa* bark tincture; *Olea europaea* leaves hydroalcoholic extract comprising oleuropein; *Coffea arabica* (green coffee beans) tincture; Vitamin D3; zinc oxide and p-coumaric acid.

Any of the compositions of this disclosure may further comprise an inert ingredient, such as for example, ethanol, starch, microcrystalline cellulose, or any combination thereof.

The compositions of this disclosure may be spray-dried. The compositions of this disclosure may be encapsulated. The compositions of this disclosure may be spray-dried and encapsulated within at least one carrier.

The compositions of this disclosure may be formulated for oral administration as a food product, beverage, juice, chewables, syrup, powder, granules, tea bag, tablet, pill, capsules, softgel capsules, liquid or drops.

The compositions of this disclosure may be formulated for a topical application as a lotion, gel, cream, ointment, hair shampoo, hair conditioner, hair spray, hair foam, soap, patch, powder, tissue or a sprayable powder.

Further aspects of this disclosure are directed to a dietary supplement or topical formulation comprising one or more of the compositions of this disclosure.

A composition according to this disclosure may comprise the *Euterpe oleracea, Tabebuia impetiginosa*, Oleuropein from dried leaves of *Olea europaea*, vitamin D3 (Cholecalciferol), L-arginine, calcium d-pantothenate and magnesium citrate. In this composition, the ingredients may be used in the following ratios:

*Euterpe oleracea* as a freeze-dried concentrate 1:4—100 mg to 300 mg;
*Tabebuia impetiginosa* extract—100 mg to 200 mg;
Oleuropein from *Olea europaea* dried leaves—50 mg to 150 mg;
Vitamin D3 (Cholecalciferol)—300 UI to 500 UI;
L-arginine—150 mg to 200 mg;
Calcium d-pantothenate—0.5 mg to 5 mg; and
Magnesium citrate—200 to 400 mg.

This composition may further comprise at least one inert ingredient. The inert ingredient may be water. This composition may be formulated in capsule form.

Further aspects of this disclosure provide a non-medicinal method for rejuvenating hair in a human subject, the method comprising administering to the human subject one or more of the compositions of this disclosure.

The methods may be performed with a composition comprising: an *Euterpe oleracea* extract comprising cyanidin 3-glycoside and/or cyanidin 3-rutinoside, an *Olea europaea* extract comprising oleuropein, a *Coffea arabica* extract, a *Tabebuia impetiginosa* extract; a micronutrient comprising zinc, and vitamin D3. In the methods, the composition may further comprise p-coumaric acid.

In the methods, one or more of the compositions of this disclosure may be administered as a dietary supplement and/or as a topical formulation. In the methods, administering of one or more of the compositions of this disclosure may lead to the downregulation of TGF-$\beta$1.

Further aspects of this disclosure relate to the use of one or more of the compositions of this disclosure in a dietary supplement and/or in a hair care product for non-medicinal treatment of hair loss in a human subject.

Further aspects of this disclosure relate to the use of any one of the compositions of this disclosure in a dietary supplement and/or topical formulation for rejuvenating hair, skin and/or nails.

BRIEF DESCRIPTION OF THE DRAWINGS

FIG. 12A is a no-treatment control; FIG. 12B is 2 mg/ml ZM-26 in capsule and testosterone; FIG. 12C is testosterone treatment; and FIG. 12D is 2 mg/ml ZM-26 in liquid form and testosterone.

FIG. 18A is a densitometry data for FIG. 18B.

FIG. 18B is a Western blot of TGF-β1 expression in male HFDP cells treated with the ZM-26 composition for 24 h.

FIG. 19A is a densitometry data for FIG. 19B.

FIG. 19B is a Western blot of TGF-β1 expression in female HFDP cells treated with with the ZM-26 composition for 24 h.

DETAILED DESCRIPTION

Figure 1B:
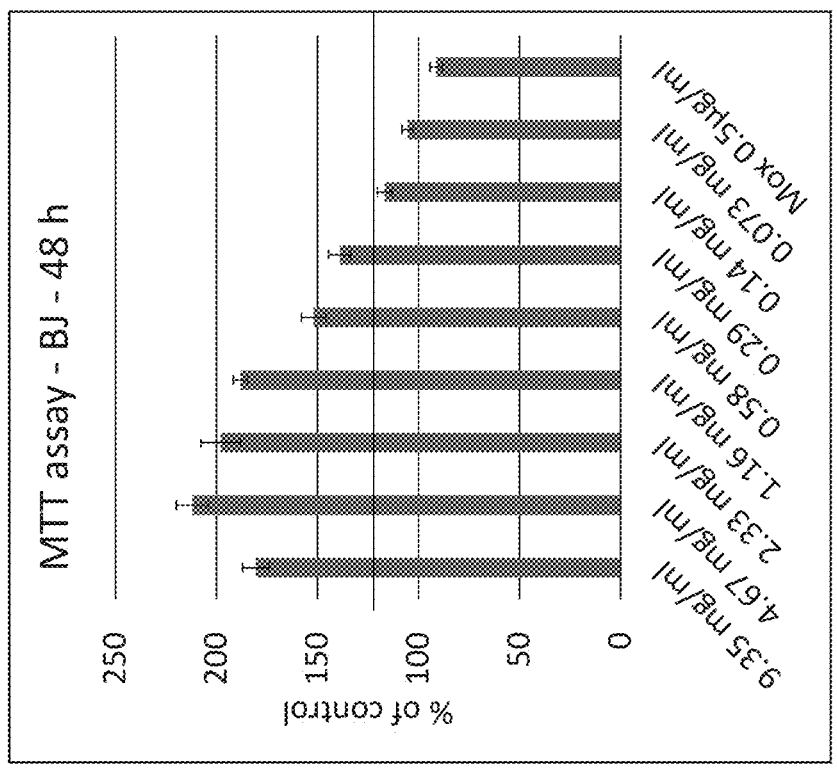
FIG. 1B is a growth curve of BJ cells treated with various concentrations of the ZM-26 composition.

Some aspects of this disclosure relate to compositions comprising:
1) One or more of the following extracts:
   a) an *Euterpe oleracea* extract comprising cyanidin 3-glycoside and/or cyanidin 3-rutinoside,
   b) an *Olea europaea* extract comprising oleuropein,
   c) a *Coffea arabica* extract, and/or
   d) a *Tabebuia impetiginosa* extract;
2) a micronutrient comprising zinc, and
3) vitamin D3 (also known and referred to interchangeably as cholecalciferol).

Some preferred compositions in this disclosure comprise a hydroalcoholic *Euterpe oleracea* extract comprising cyanidin 3-glycoside and/or cyanidin 3-rutinoside, a hydroalcoholic *Olea europaea* extract comprising oleuropein and a hydroalcoholic *Coffea arabica* green beans extract. These compositions may further comprise a micronutrient comprising zinc and/or vitamin D3.

Some preferred compositions in this disclosure comprise a hydroalcoholic *Euterpe oleracea* extract comprising cyanidin 3-glycoside and/or cyanidin 3-rutinoside, a hydroalcoholic *Olea europaea* extract comprising oleuropein, a hydroalcoholic *Coffea arabica* green beans extract, a hydroalcoholic *Tabebuia impetiginosa* extract, a micronutrient comprising zinc and vitamin D3.

In the compositions provided in this disclosure, the extracts may be used in the following ratios: about 100 parts of the *Euterpe oleracea* extract by volume; about 3 to 10 parts of the *Olea europaea* extract by volume; about 3 to 10 parts of the *Coffea Arabica* extract by volume; and about 0 to 4 parts of the *Tabebuia impetiginosa* extract by volume. In any of these compositions, the extracts may be used in the following volume ratios: *Euterpe oleracea:Olea europaea:Coffea Arabica:Tabebuia impetiginosa:* 100:6:6:2.

The term "about" in this disclosure is used in its common meaning and means "approximately." A person of skill will understand that "about" is within 10% of a stated value, preferably within 5%, more preferably within 1%, and most preferably within 0.5%. For example, "about 100" means 100±10; preferably 100±5; more preferably 100±1, and most preferably 100±0.5.

In the compositions of this disclosure, the ingredients may be used in the following amounts. Per 100 to 150 mg of a *Euterpe oleracea* extract, the other ingredients may be used in the following amounts: from 55 to 105 mg of a *Tabebuia impetiginosa* extract, from 25 to 80 mg of an *Olea europaea* extract, from 50 to 100 mg of a *Coffea arabica* extract, from 5 to 20 mg of a micronutrient comprising zinc, from about 200 to 2000 IUs of Vitamin D3, from 0 to 100 mg of a magnesium micronutrient, such as for example magnesium citrate, and from 0 to 10 mg of a calcium micronutrient such as for example calcium d-pantothenate. The *Euterpe oleracea* extract may be a freeze-dried concentrate. The *Euterpe oleracea* extract may be a freeze-dried concentrate concentrated in a range from about 2:1 to about 10:1. Preferably, the *Euterpe oleracea* extract is a freeze-dried Acai berry concentrate in a range from about 4:1 to about 5:1.

A composition in this disclosure may further comprise p-coumaric acid. Various concentrations of p-coumaric acid are suitable. In some compositions, p-coumaric acid is used in an amount from 0.2% to 3% by weight of the total weight of the composition. For example, from 0.2 g to 3 g of p-coumaric acid may be used if the total weight of the composition is 100 g.

Some of the compositions in this disclosure comprise the micronutrient comprising zinc in an amount from 0.2% to 5% by weight of the total weight of the composition. The total amount of vitamin D3 in the compositions may vary. Typically, from 100 to 2000 international units (IUs) of vitamin D3 may be used per a daily dosage.

The compositions of this disclosure may be prepared in lyophilized forms or in liquid form.

The compositions of this disclosure may be spray-dried and further comprise one or more of inert ingredients serving as a carrier. Suitable inert ingredients include ethanol, starch, modified starch, microcrystalline cellulose, or any combination thereof. The compositions of this disclosure may be mixed with a carrier, spray-dried and encapsulated with the carrier. Suitable carriers include any of the carriers typically used for encapsulation in spray-drying. Suitable carriers comprise microcrystalline cellulose (also known as cellulose gel), starch, modified starch, or any combination thereof.

The compositions of this disclosure can be used for a non-medicinal treatment of hair loss. In this disclosure, the hair loss is treated in a human subject, if the human subject visually observes after using continuously one or more of the compositions of this disclosure for at least 3 months, and preferably for at least 4 to 6 months, any of the following: at least a partial delay in hair shedding, stimulation of hair growth such that hair grows longer, and/or stimulation of re-growth of hair in balding areas of the scalp.

The compositions can be also used for nourishing and rejuvenating hair, skin and/or nails. Any visual improvement in hair texture and/or length as observed by a human subject consuming and/or topically applying one or more of the compositions provided in this disclosure is referred to as hair rejuvenation. On visual inspection, hair can become thicker, shinier, less frizzy, less fragile and/or start to grow faster. On visual inspection, skin can start to appear more supple, more elastic, less dull. On visual inspection, nails can start to grow faster and become stronger and less brittle. Typically, these improvements can be detected after at least 2 months, and preferably after at least 4 to 6 months, of continuous use of one or more compositions of this disclosure.

The compositions of this disclosure downregulate expression of TGF-β1 protein. The compositions of this disclosure stimulate cell proliferation. The compositions of this disclosure protect cells from the oxidative stress. The compositions of this disclosure may be used for protecting skin and/or hair follicles from the oxidative stress and inflammation.

Extracts for the compositions of this disclosure may be obtained from one or more plant materials. A plant material may include, but is not limited to, a leaf, fruit, vegetable, berry, root, flower, seed, nut, bean, steam, branch, trunk, wood bark and/or any combination thereof. The plant material may be a freshly harvested plant material, and/or it can be a harvested and dried plant material. Any of plant materials may be further frozen. A plant material may be lyophilized and/or otherwise concentrated.

Some extracts may be obtained by mechanically disrupting one or more plant materials, for example by using a blender, and making a puree and/or by pressing a juice from one or more plant materials. Any of these extracts may be then concentrated, for example by lyophilization. Some extracts may be obtained by mixing one or more plant materials or plant material concentrates with a solvent, and further extracting soluble substances from the plant materials. A solvent may be water. Suitable solvents include polar protic solvents which can be mixed with water. Suitable solvents include alcohols, mixtures of alcohols in water, or water. Preferred alcohols include ethanol and isopropanol. Ethanol and mixture of ethanol with water are preferred solvents. Preferred solvents include a 30% (v/v) to 90% (v/v) solution of ethanol or other alcohol in water. Other solvents, such as vinegar, may be also used. Preferred extracts in this disclosure are hydroalcoholic extracts which are prepared by extracting soluble substances from a plant material and/or plant material concentrate with a mixture of ethanol in water.

A preferred plant material for an *Euterpe oleracea* extract comprises berries of the plant, referred to in this disclosure as acai berries. A preferred plant material for an *Olea europaea* extract comprises leaves of the plant. The leaves may be dried leaves. A preferred plant material for a *Coffea arabica* extract comprises green beans of the plant. The coffee beans may be immature coffee beans which have not been roasted or mature coffee beans which have not been roasted. Any of the unroasted coffee beans either immature or mature are referred in this disclosure as green coffee beans. A preferred plant material for a *Tabebuia impetiginosa* extract comprises bark of the plant.

A mixture of one or more plant materials with one or more solvents may be heated, and optionally it may be boiled, and optionally it may be steeped, and optionally it may be filtered and/or percolated. In alternative, the mixture may be extracted at room temperature (21° C.) or in cold, which is at any temperature in the range from 0° C. to 21° C. The process of extraction may be carried on for a period of time from 1 minute to several days, depending on the plant material and solvent and some other conditions. The ratios of the plant material to the solvent may be in a range of 1:0.5 to 1:100 (w/v). For example, for 1 g of the plant material from 0.5 ml to 100 ml of the solvent may be used. The plant material may be milled, chopped, powdered, pressed, lyophilized and/or concentrated.

After the extraction with the solvent has been completed, an extract may be further concentrated by evaporation, lyophilization and/or dried into a powder or paste. An extract may be further diluted with water and/or mixed with other suitable excipients, e.g. ethanol, as needed.

The term "extract" is understood in this disclosure broadly and includes any product comprising a substance obtained from one or more plant materials. The extract may be a lyophilized puree or juice from one or more plant materials. The extract may be obtained by extracting one or more plant materials with at least one solvent. Examples of the substances include, but are not limited to, chlorogenic acid, oleuropein, cyanidin 3-glycoside and cyanidin 3-rutinoside and any other chemical compounds and mixtures obtained from one or more plant materials. The extract may be in a powder form or as a tincture. It may be an alcoholic tincture comprising ethanol. In alcoholic tinctures, a preferred concentration of ethanol is from about 5% (v/v) to about 30% (v/v) of the composition total.

The extraction may include, but is not limited to, any one of the of following: pressing, homogenizing, heating, cooling, steeping, boiling, percolating, filtering, centrifuging, evaporating, drying, separating into phases, and any combination thereof.

A preferred *Euterpe oleracea* extract is an Acai berry extract comprising cyanidin 3-glycoside and/or cyanidin 3-rutinoside. These extracts may be obtained by extracting Acai berries or Acai berries lyophilized concentrate with 1 to 10 volumes of 70% (v/v) to 90% (v/v) ethanol at room temperature for a period of time, i.e. from 30 minutes to 24 hours. The extract may be concentrated by evaporation. Suitable *Euterpe oleracea* extracts include those which comprise at least 20 mg of cyanidin 3-glucoside per 100 g of the dry weight of the starting extraction material. Suitable *Euterpe oleracea* extracts also comprise at least 30 mg of cyanidin 3-rutinoside per 100 g of the dry weight of the starting extraction material.

Genus *Euterpe* includes at least the following eight plants: *E. broadwayi, E. caatinga, E. edulis, E. longibracteata, E. luminosa, E. oleracea* and *E. precatoria*. Any of these plants are suitable, but *E. oleracea* is a preferred species.

At least in some embodiments, the compositions of this disclosure may comprise synthetic cyanidin 3-rutinoside and/or synthetic cyanidin 3-glucoside in addition to, or instead of an *Euterpe oleracea* extract.

A preferred *Olea europaea* extract is a hydroalcoholic extract of olive leaves. The extract comprises oleuropein. The extract may be obtained by percolating leaves, such as dry leaves for example, in 1 to 10 volumes of 50% ethanol and 50% distilled water (v/v) at room temperature. Other concentrations for ethanol mixtures, i.e. from 50% to 90% of ethanol in distilled water (v/v) may be also used. The extract may be concentrated. Suitable extracts include those which comprise at least 10% of oleuropein. In some embodiments, the compositions of this disclosure may comprise synthetic oleuropein in addition to, or instead of an *Olea europaea* extract.

A preferred *Coffea arabica* extract is a hydroalcoholic extract of unroasted green coffee beans. The extract may be obtained by extracting the green coffee beans in 1 to 10 volumes of an ethanol/water mixture. Suitable concentrations for ethanol mixtures include from 50% to 90% of ethanol in distilled water (volume by volume, abbreviated through this application as v/v).

A preferred *Tabebuia impetiginosa* extract is a hydroalcoholic extract of the plant bark. The extract may be obtained by extracting the bark in 1 to 10 volumes of an ethanol/water mixture. Suitable concentrations for ethanol mixtures include from 50% to 90% of ethanol in distilled water (v/v).

The compositions of this disclosure may comprise a micronutrient comprising zinc. Suitable zinc micronutrients include, but are not limited to, zinc oxide and/or salts such as for example, zinc picolinate.

The compositions of this disclosure may comprise vitamin D3.

The compositions of this disclosure may further comprise one or more of amino acids, one or more additional vitamins, one or more additional micronutrients, or any combination thereof.

Suitable amino acids include, but are not limited to, tryptophan, glutamine, aspartic acid, arginine, ornithine, lysine, tyrosine, taurine, histidine, phenylalanine, methionine, or any combination thereof. One preferred amino acid is L-arginine.

In addition to or instead of zinc, the compositions of this disclosure may further comprise one or more of micronutrients, which may include, but are not limited to, calcium, magnesium, iron, copper, iodine, potassium, and any combination thereof. Micronutrients may be supplied as a compound such as a salt. Preferred micronutrients include compounds comprising calcium and/or magnesium. Calcium d-pantothenate is one preferred salt. Magnesium citrate is another preferred salt. Some compositions comprise calcium d-pantothenate and magnesium citrate, and optionally, other micronutrients as well.

Additional vitamins include, but are not limited to, vitamin A, vitamin E, vitamin C, vitamin B1, vitamin B2, vitamin B3, vitamin B5, vitamin B6, vitamin B9, vitamin B12, and any combination thereof.

One preferred composition in this disclosure is referred to as ZM-26. This composition comprises the following active ingredients: an *Euterpe oleracea* extract comprising cyanidin 3-glucoside and cyanidin 3-rutinoside; *Tabebuia impetiginosa* extract; *Olea europaea* dried leaves extract comprising oleuropein; *Coffea arabica* (green coffee beans) extract, Vitamin D3 (Cholecalciferol); calcium d-pantothenate; magnesium citrate; and zinc picolinate. The ZM-26 composition may further comprise inert ingredients, such as for example, ethanol, starch and/or microcrystalline cellulose. The ZM-26 composition may be used for non-medicinal hair-loss treatment and/or for rejuvenation of hair and/or skin and nails in any effective amount. A preferred effective amount of the ZM-26 composition is any amount sufficient to downregulate expression of TGF-β1 protein. The ZM-26 composition may be consumed orally as a dietary supplement.

In the ZM-26 composition, the active components may be used in the following ratios by weight as shown in Table 1.

TABLE 1

| Component | Amounts | Preferred Amount |
| --- | --- | --- |
| *Euterpe oleracea* extract concentrated 1:4 | 100 to 150 mg | 125 mg |
| *Tabebuia impetiginosa* extract | 55 to 105 mg | 80 mg |
| *Olea europaea* dried leaves extract | 25 to 80 mg | 55 mg |
| Cholecalciferol (Vitamin D3) | 200-2000 IU | 1000 IU |
| Calcium d-pantothenate | 0-10 mg | 5 mg |
| Magnesium citrate | 0-100 mg | 85 mg |
| Zinc picolinate | 5-20 mg | 15 mg |
| *Coffea arabica* (green coffee beans) extract | 50-100 mg | 85 mg |

A daily dosage of the ZM26 composition may vary. Typically, from 0.5 mg to 500 mg of the ZM26 composition may be taken per one dosage. From one to 3 or 4 dosages may be taken daily.

Another preferred composition provided in this disclosure comprises the following active ingredients: an Acai berry (*Euterpe oleracea*) extract comprising cyanidin 3-glucoside and cyanidin 3-rutinoside; a *Tabebuia impetiginosa* bark extract; an Olive leaf (*Olea europaea*) extract comprising oleuropein; a *Coffea arabica* (green coffee beans) extract; Vitamin D3 (cholecalciferol); zinc oxide and p-coumaric acid. This composition may further comprise inert ingredients, such as for example, ethanol, starch and/or microcrystalline cellulose. The composition may be used for non-medicinal treatment of hair loss and/or rejuvenation of hair and/or skin and nails in any effective amount. A preferred effective amount of the composition is any amount sufficient to downregulate expression of TGF-β1 protein. In this composition, the components may be mixed in the following ratios as shown in Table 2.

TABLE 2

| Component | Ratios/Amounts | Exemplary Composition |
| --- | --- | --- |
| *Euterpe oleracea* (Acai berries)hydroalcoholic extract comprising cyanidin 3-glucosideandcyanidin 3-rutinoside, 5:1concentrate | 5 parts by volume | 5 ml of 10X concentrated extract |
| *Tabebuia impetiginosa* bark tincture | 0.1 part by volume | 0.1 ml of 10X concentrated extract |
| *Olea europaea* (olive leaves) hydroalcoholic extract comprising oleuropein | 0.3 parts by volume | 0.3 ml of 10X concentrated extract |
| *Coffea arabica* (unroasted green coffee beans) tincture | 0.3 parts by volume | 0.3 ml of 10X concentrated extract |
| Cholecalciferol (Vitamin D3) | 1 to 20 mg | 10 mg |
| Zinc oxide | 1 to 10 mg | 5 mg |
| p-coumaric acid | 0 to 20 mg | 10 mg |

Typically, from 0.1% to 10% of the exemplary composition shown in Table 2 may be administered per one dosage.

In one exemplary embodiment, a composition of the present disclosure may comprise:
1. *Euterpe oleracea* as a freeze-dried concentrate 1:4
2. *Tabebuia impetiginosa* extract
3. Oleuropein from *Olea europaea* dried leaves
4. Vitamin D3 (Cholecalciferol)
5. L-arginine
6. Calcium d-pantothenate
7. Magnesium citrate In one exemplary embodiment, a composition of the present disclosure may comprise the following components in the following amounts:
1. *Euterpe oleracea* as a freeze-dried concentrate 1:4—100 mg to 300 mg;
2. *Tabebuia impetiginosa* extract—100 mg to 200 mg;
3. Oleuropein from *Olea europaea* dried leaves—50 mg to 150 mg;
4. Vitamin D3 (Cholecalciferol)—300 UI to 500 UI;
5. L-arginine—150 mg to 200 mg
6. Calcium d-pantothenate—0.5 mg to 5 mg
7. Magnesium citrate—200 to 400 mg In vitro tests have shown that the compositions of this disclosure are likely not a DHT blocker. Without wishing to be bound by this theory, it is postulated that the mechanism of action of the compositions may be through one or more antioxidant, vasorelaxant and anti-inflammatory activities by one or more of the components of the compositions of this disclosure.

The compositions of this disclosure may also contain one or more inert ingredients, such as water and/or ethanol (for a liquid composition), or starches or microcrystalline cellulose (for a solid composition). The compositions may be formed by mixing the active ingredients with the inert ingredients, as is well-known in the art.

This disclosure also provides a method, comprising administering to a human subject who would benefit from this administration a beneficial amount of any of the foregoing compositions. For instance, if the composition is prepared in capsule form, a human subject may ingest one or several capsules, for example two capsules, daily. The capsules may comprise from 0.5 mg to 500 mg of one or more compositions described in this disclosure.

Alternatively, in some embodiments, the composition may be prepared in the form of a ready-made drink, or as a powder that can be combined with water or juice and then ingested by an individual. In some embodiments, the method may include administration of the composition to an individual daily, multiple times per day, for example twice daily, or less than daily.

In some embodiments, a human subject is experiencing hair loss, and one or more compositions of this disclosure a r e administered in order to facilitate hair regrowth and/or to ameliorate a further hair loss. The hair loss may be a side effect of a treatment, such as for example, a cancer treatment. However, any human subject wishing to rejuvenate his/her hair may benefit from the compositions of this disclosure. The compositions of this disclosure may be also used by individuals wishing to improve the appearance of hair and/or nails and/or skin.

The compositions of this disclosure may be formulated as a dietary supplement or as a topical formulation. The dietary supplement may be formulated for oral administration such as a food product, beverage, juice, chewables, syrup, powder, granules, tea bag, tablet, pill, powder, capsules, softgel capsules, liquid or drops. The dietary supplement may further comprise one or more of inert ingredients selected from a flavoring agent, sweetener, bulking agent, water, ethanol, pH stabilizer, fibers, starch, microcrystalline cellulose, and/or other inert ingredients typically used in dietary supplements. The dietary supplements may comprise from 0.5 mg to 500 mg of one or more compositions described in this disclosure per one administration dosage.

The compositions of this disclosure may be formulated for a topical administration. A topical formulation may be formulated as a hair care or body care product such as a lotion, gel, cream, ointment, hair shampoo, hair conditioner, soap, hair foam, hair spray, a patch, powder, or a sprayable powder. As is well known to a person of skill, the topical formulations may comprise additional ingredients typical for hair care or body care products. Topical formulations may comprise from 0.2 mg/ml to 200 mg/ml of one or more of compositions of this disclosure.

In further aspects, this disclosure provides non-medicinal methods for treating hair loss in a human subject. The methods comprise administering to the human subject one or more of the compositions of this disclosure. The compositions may be administered orally, i.e. as a dietary supplement, and/or topically, i.e. as a hair care product, by applying the composition to the human subject's scalp.

The compositions of this disclosure can be used for treating either male or female human subjects. The compositions of this disclosure can be used for treating multifactorial alopecia, including non-androgenic forms. The compositions of this disclosure may be also used in other treatments whether the level of TGB-β1 protein needs to be reduced and/or when cells need to be rescued from the oxidative stress.

In further aspects, this disclosure provides non-medicinal methods for improving the appearance of skin, hair and/or nails. The methods comprise administering to the human subject, one or more of the compositions of this disclosure. The compositions may be administered orally as a dietary supplement and/or topically by applying the composition to the human subject's scalp.

Other applications may include methods for reducing the oxidative stress and/or inflammation in a human subject by administering to the human subject one or more of the compositions of this disclosure.

For oral applications, an effective amount of the composition will vary and depend on a particular application. Typically, between 0.5 mg to 500 mg of one or more compositions described in this disclosure may be administered at least once daily, at least twice daily, at least three times daily, or at least four times daily. Typically, a human subject may consume one or more compositions of this disclosure for a period of time, such for example, from two weeks to three to four months.

In topical applications, one or more compositions of this disclosure are applied to the human subject's scalp. For topical applications, one or more of the compositions of this disclosure may be formulated as a hair care product. Topical formulations may comprise from 0.2 mg/ml to 200 mg/ml of one or more of compositions of this disclosure. The topical applications may be daily or weekly or monthly.

Without wishing to be bound by a theory, the present compositions are based on synergistic effects of the plant and mineral constituents acting together on cell proliferation of hair tissue, rescuing damaged cells from the oxidative stress and decreasing the expression of TGF-β1 protein.

Figure 1A:
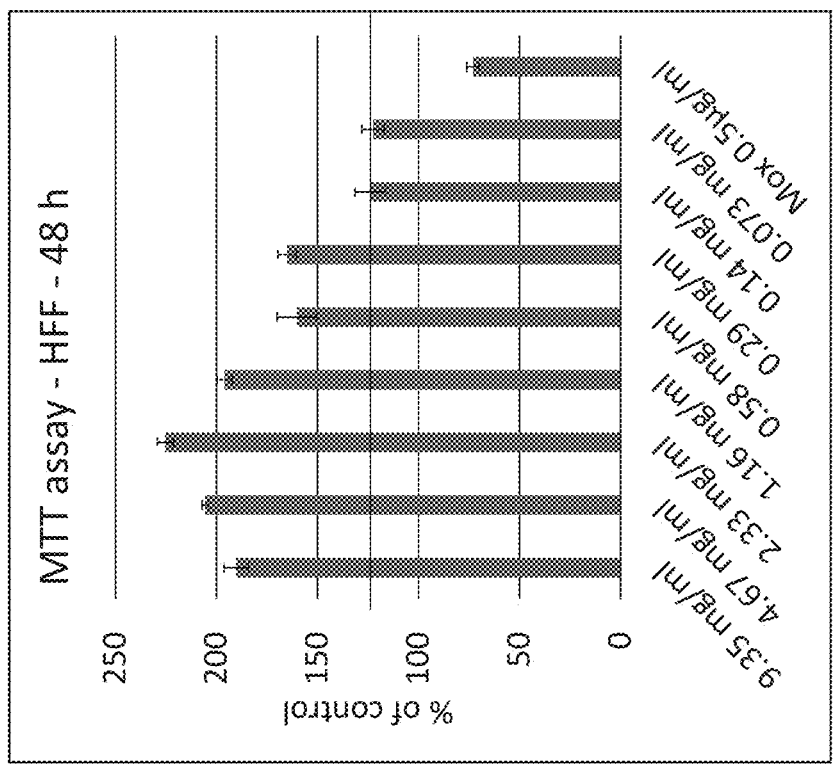
FIG. 1A is a growth curve of HFF cells treated with various concentrations of the ZM-26 composition.

Referring to FIGS. 1A and 1B, they report results of a proliferative (MTT) assay in human foreskin fibroblasts (HFF) cells (FIG. 1A) and BJ fibroblast cell line (FIG. 1B). As can be seen in FIGS. 1A and 1B, there is a robust increase in cell proliferation for cells treated with the ZM-26 composition in concentrations 9.35 to 1.16 mg/ml, a moderate increase in proliferation of cells treated with the ZM-26 composition in concentrations 0.58 and 0.29 mg/ml, and a slight increase for cells treated with the ZM-26 composition in concentrations 0.14 and 0.07 mg/ml. The effect is observed for both cell types, BJ cells (FIG. 1B) and HFF cells (FIG. 1A). In parallel studies, minoxidil, an antihypertensive vasodilator medicine used to treat hair loss, failed to promote cell proliferation in these cells.

Figure 2:
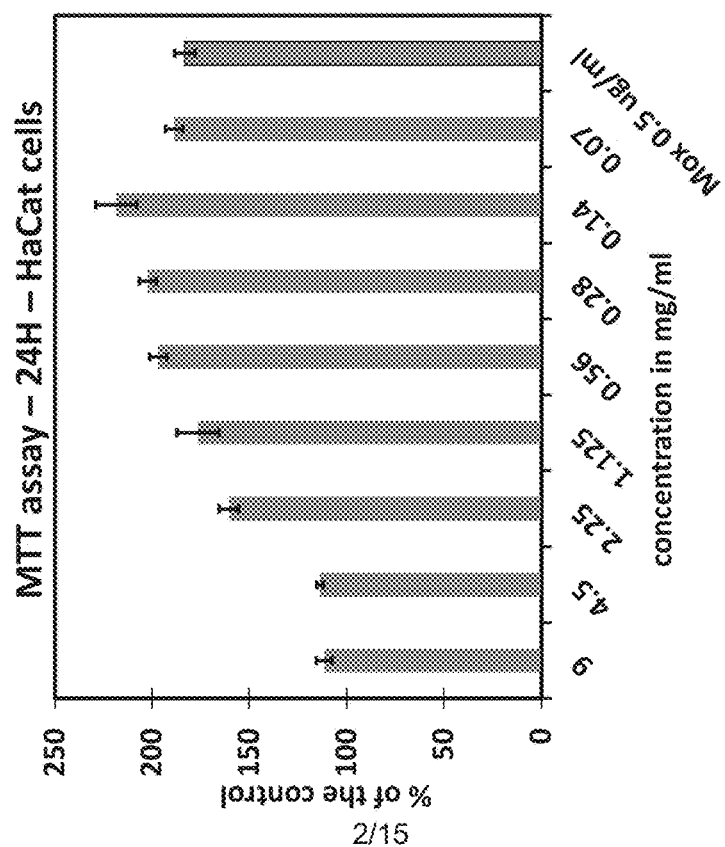
FIG. 2 is a growth curve of HaCat (hair bulb) cells treated for 24 h with various concentrations of the ZM-26 composition.

Referring to FIG. 2, it reports results of a cell proliferation assay and shows that the ZM-26 composition stimulates proliferation of HaCat (hair bulb) cells. A specific dose-response curve is observed in keratinocytes cells (HaCaT) when treated with the ZM-26 composition for 24 hours. The proliferation effect ranged from 2.25 mg/ml to 0.07 mg/ml, with the maximum effect at 0.14 mg/ml. It is noteworthy that very low concentrations were also able to promote a remarkable cell proliferation.

Figure 3:
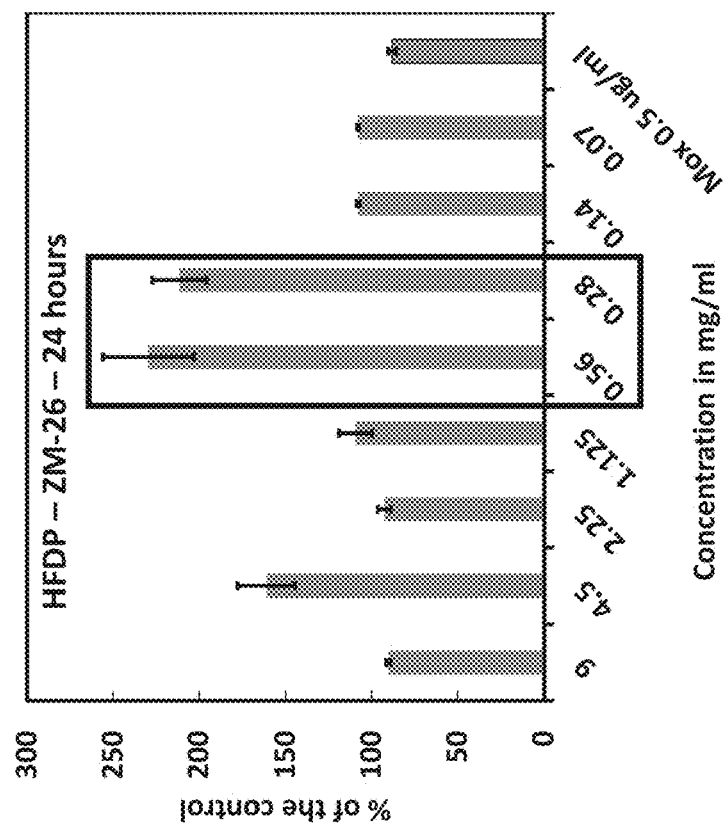
FIG. 3 is a growth curve of human follicle derma papilla cells (HFDP) treated with various concentrations of the ZM-26 composition for 24 h.

Referring to FIG. 3, it reports results of a cell proliferation assay and shows that the ZM-26 composition stimulates proliferation in human follicle derma papilla cells (HFDP). The HFDP cells used in this study are from a 26-year old male donor. There was a robust increase in cell proliferation in cells treated with the ZM-26 composition in concentrations 0.56 to 0.28 mg/ml. A similar proliferation effect was observed in HaCat cells. In control, minoxidil failed to promote cell proliferation. See the Mox 0.5 ug/ml bar in FIG. 3.

Figure 4:
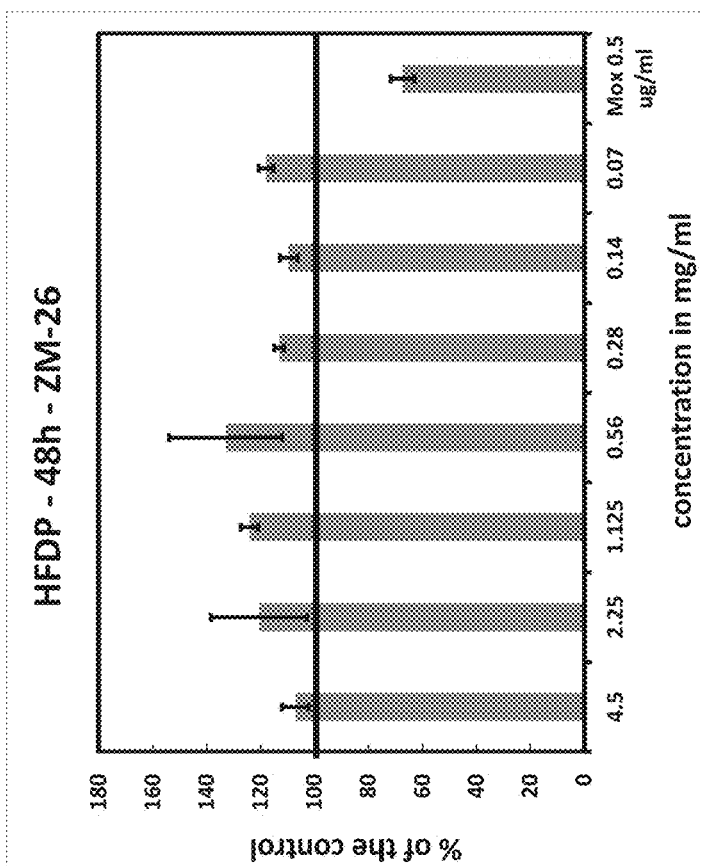
FIG. 4 is a growth curve of human follicle derma papilla cells (HFDP) treated with various concentrations of the ZM-26 composition for 48 h.

Referring to FIG. 4, it reports results of a cell proliferation assay and shows that the ZM-26 composition should be re-administered daily in order to maintain the proliferative effect. In this study, HFDP cells were treated with the ZM-26 composition for 48 h in order to assess whether a prolonged single dose treatment would improve the proliferation effect observed in HFDP cells in 24 hours. The results show no improvement, instead, a proliferation decrease is observed when compared with the 24 h treatment, suggesting that daily doses are needed in order to maintain the proliferative effect in these cells. In control, the minoxidil treatment for 48 h caused cell death. See the Mox 0.5 ug/ml bar in FIG. 4.

The compositions of this disclosure stimulate cell proliferation. Yet, it was also discovered that the compositions of this disclosure neutralize the oxidative stress and protect cells from oxidative damage and death.

When free radicals are not inhibited by antioxidant molecules within the body, the oxidative damage accumulates, contributing to and causing effects of aging and further impairment of the antioxidant defense system. A compound called 2,2'-Azobis(2-amidinopropane)dihydrochloride (AAPH) can be used in order to module the oxidative stress conditions in cells, mimicking the damage caused by accumulation of free radicals.

Figure 5:
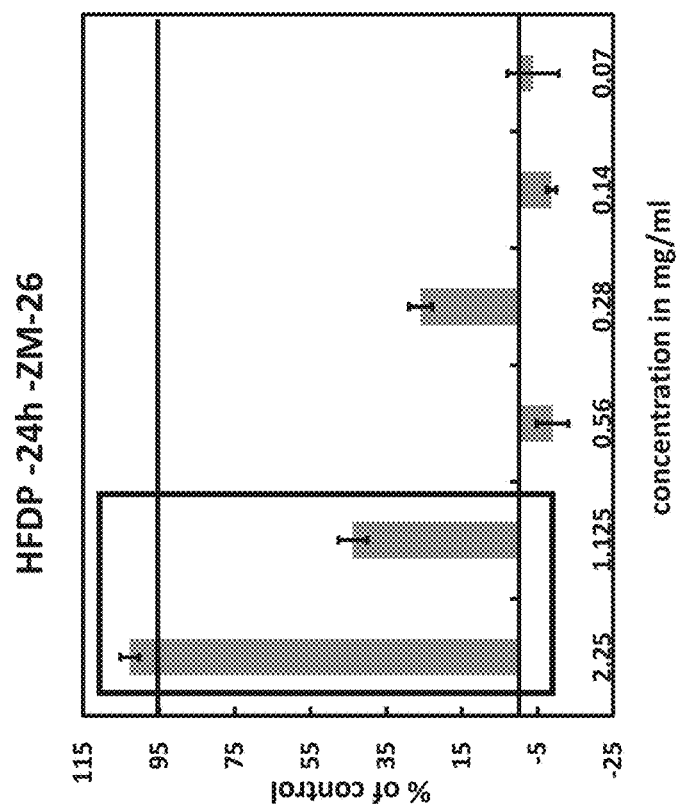
FIG. 5 shows that the ZM-26 composition rescues cells from oxidative stress caused by AAPH.

Referring to FIG. 5, it reports results of an oxidative stress test and shows that the ZM-26 composition can rescue cells from the oxidative stress. Treatment with 10 mM of AAPH for 24 hours was toxic to HFDP cells, causing an increase in cell death. However, co-treatment with 1.12 and 2.25 mg/ml of the ZM-26 composition was enough to overcome the toxic conditions generated by AAPH and rescue cell from the oxidative stress through cell growth. Interestingly, the treatment with 2.25 mg/ml of the ZM-26 composition was protective to the extent that almost no damage was observed.

Several proteins are known to affect hair proliferation. Upregulation of TGF-β1 is related to hair loss. TGF-β1 is a member of the cytokine super-family in mammals that contains nearly 30 members. These dimeric proteins regulate proliferation and apoptosis in many cell types and have a central role in triggering inflammation that is associated with hair follicle miniaturization, fibrosis (rigidification), and its eventual loss.

Figure 6B:
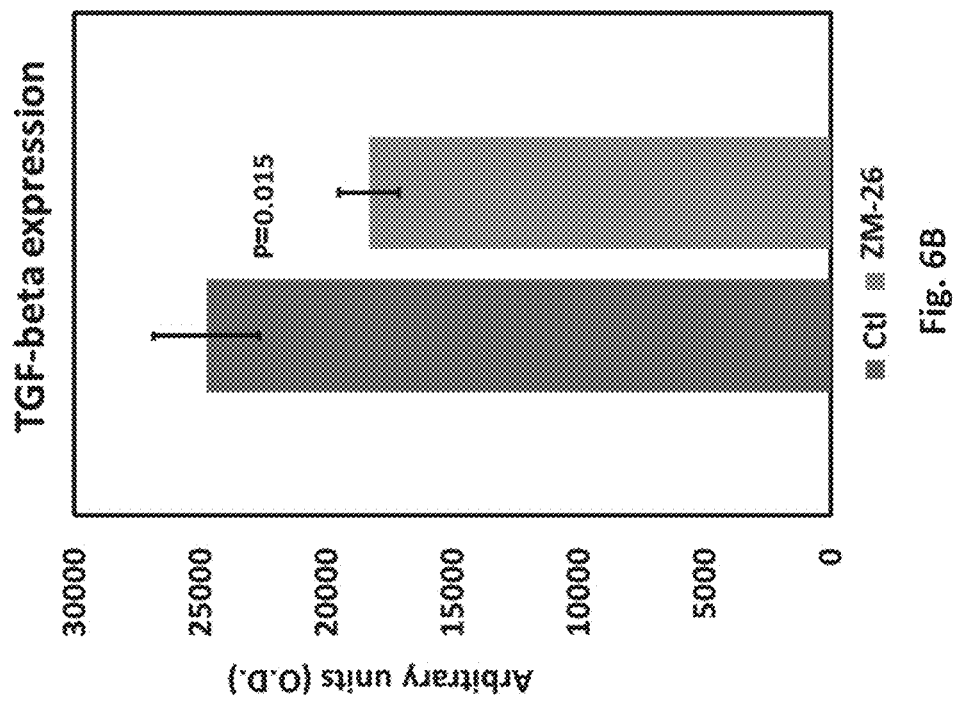
FIG. 6B is a densitometry analysis of the Western blot in FIG. 6A.
Figure 6A:
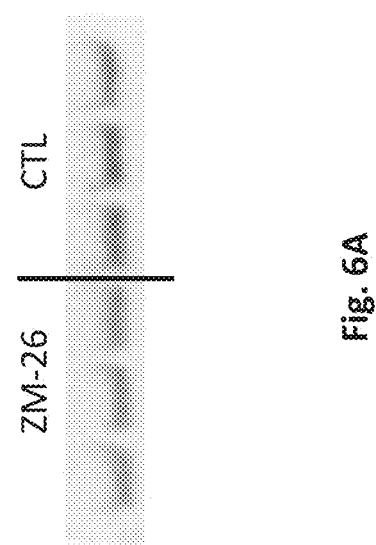
FIG. 6A is a Western blot analysis showing that the ZM-26 composition inhibits TGF-$\beta$1 expression.
Figure 7B:
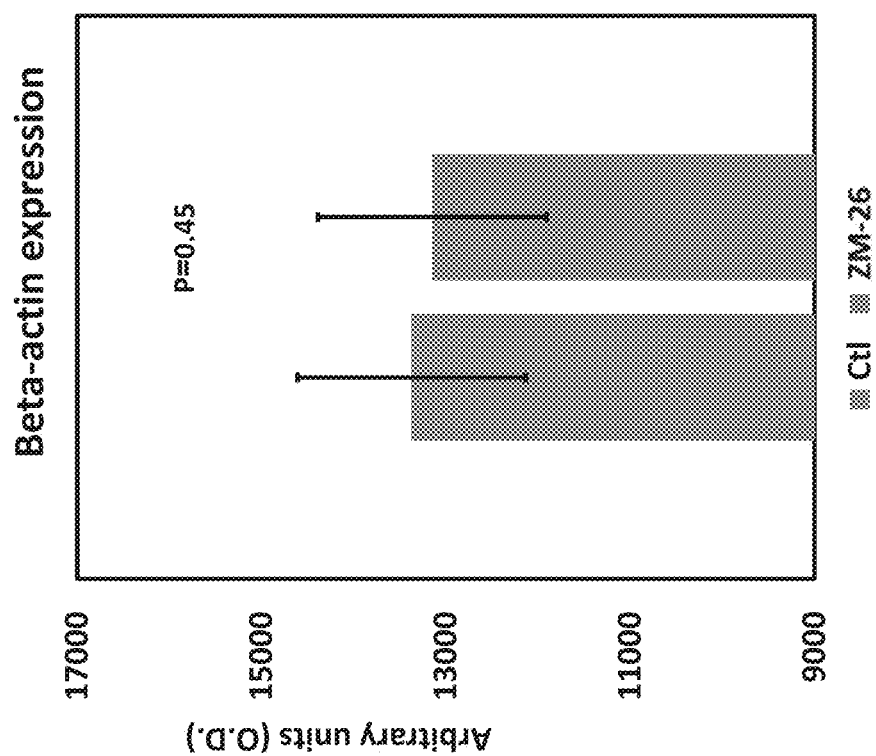
FIG. 7B is a densitometry analysis of the Western blot in FIG. 7A.
Figure 7A:
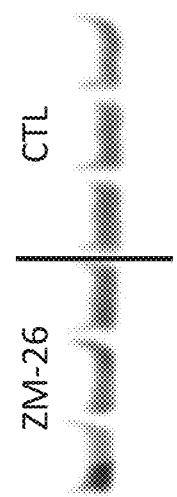
FIG. 7A is a control Western blot with beta-actin for the protein load of FIG. 6A.

Referring to FIGS. 6A and 6B, they report results of TGF-β1 protein expression in HFDP cells. As can be seen in FIG. 6A, the ZM-26 composition inhibits TGF-β1 protein expression, as shown by Western blot analysis. FIG. 6B is a densitometry data for Western blot of FIG. 6A. FIG. 7A is a control Western blot for beta-actin, showing the protein load per lane and FIG. 7B is a densitometry data for FIG. 7A.

Figure 8B:
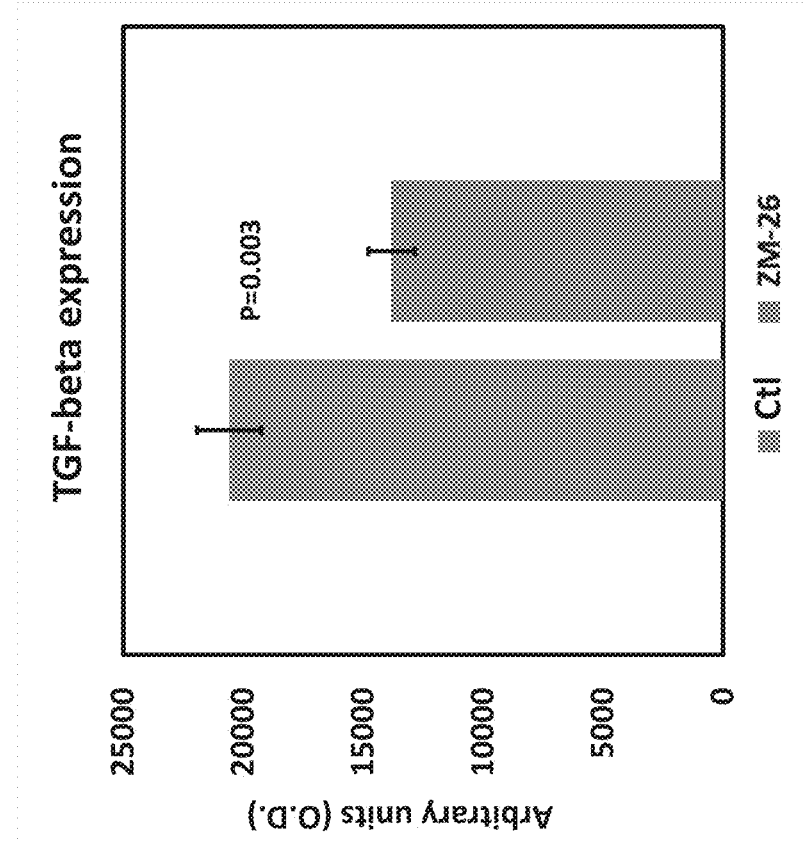
FIG. 8B is a densitometry analysis of the Western blot in FIG. 8A.
Figure 8A:
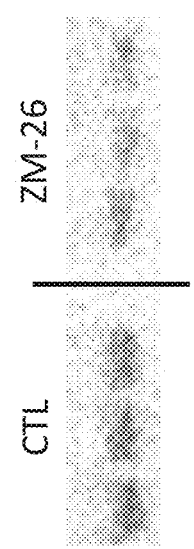
FIG. 8A measures TGF-$\beta$1 expression in cells treated with the ZM-26 composition.
Figure 9B:
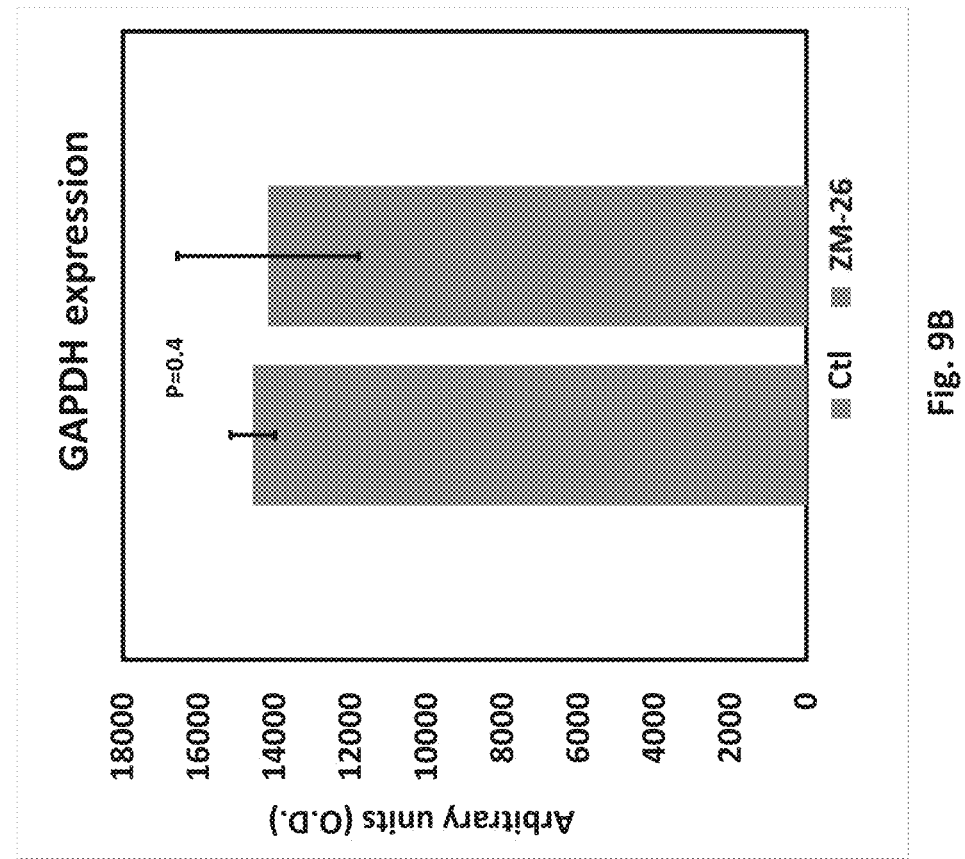
FIG. 9B is a densitometry analysis of the Western blot in FIG. 9A.
Figure 9A:
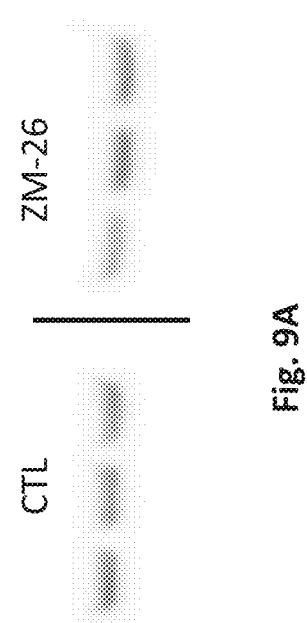
FIG. 9A is a control for the protein load of FIG. 8A.

Referring to FIGS. 8A and 8B, they report results of TGF-β1 protein expression in HaCat cells. As can be seen in FIG. 8A, the ZM-26 composition inhibits TGF-β1 protein expression, as shown by Western blot analysis. FIG. 8B is a densitometry data for FIG. 8A. FIG. 9A is a control Western blot showing the protein load per lane and FIG. 9B is a densitometry data for FIG. 9A.

Figure 10B:
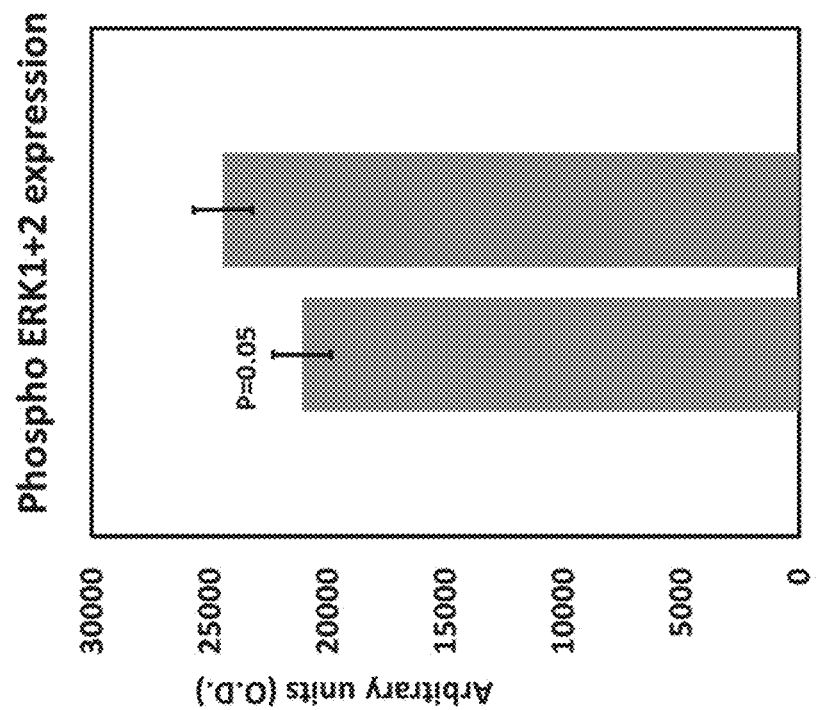
FIG. 10B is a densitometry analysis of the Western blot in FIG. 10A.
Figure 10A:
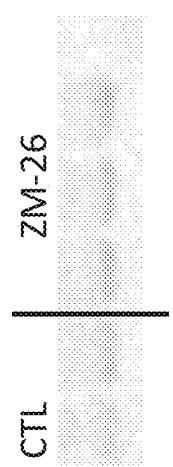
FIG. 10A is a Western blot analysis for phosphorylated ERK1+2 in cells treated with the ZM-26 composition.

Referring to FIGS. 10A (Western blot) and 10B (densitometry data for FIG. 10A), they detect accumulation of phosphorylated ERK1+2 protein in HFDP cells treated with the ZM-26 composition. This data supports a conclusion that the compositions of this disclosure stimulate cell proliferation through the ERK pathway.

Figure 11:
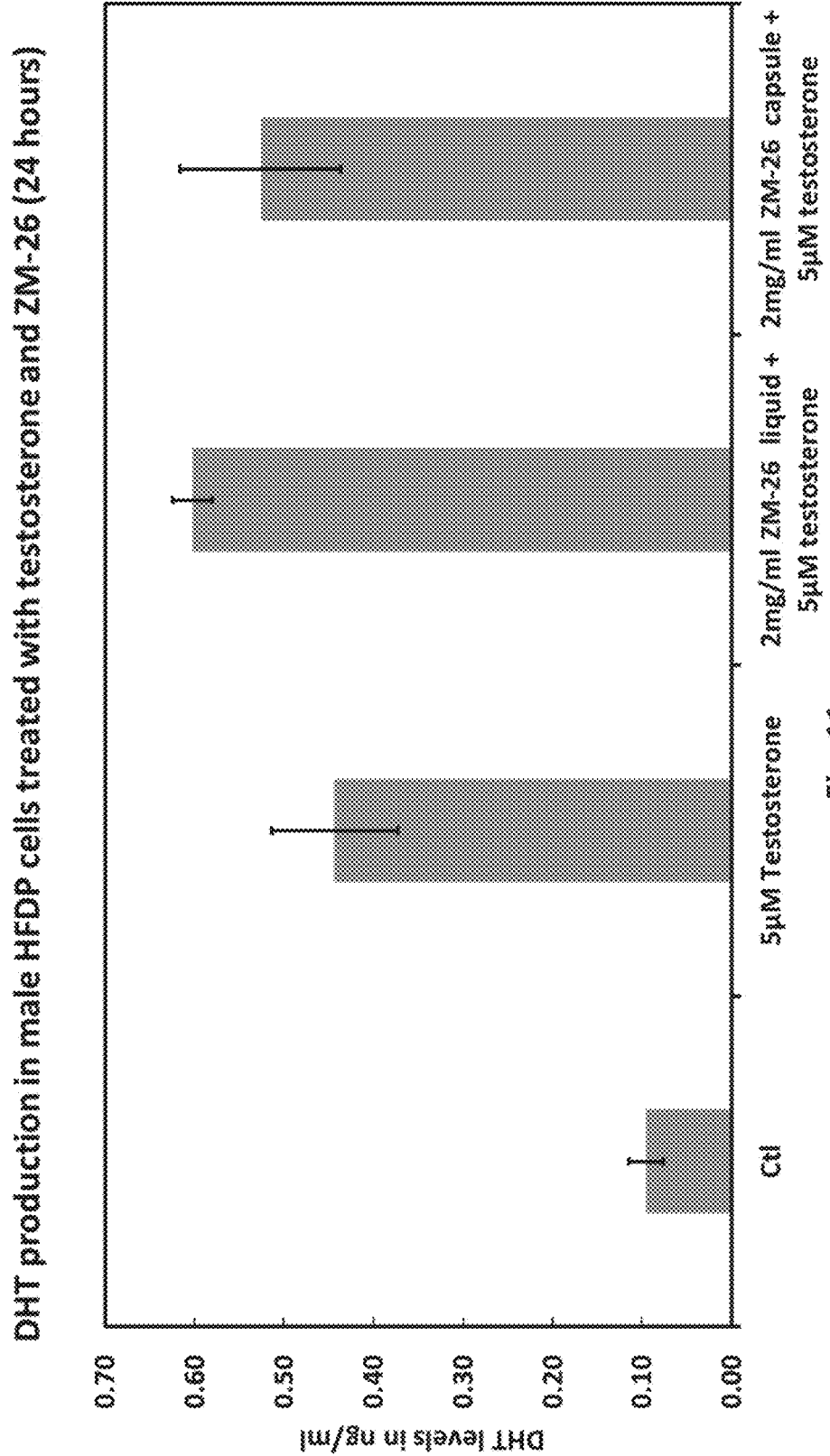
FIG. 11 reports DHT production in male HFDP cells treated with testosterone and the ZM-26 composition.
Figure 12A:
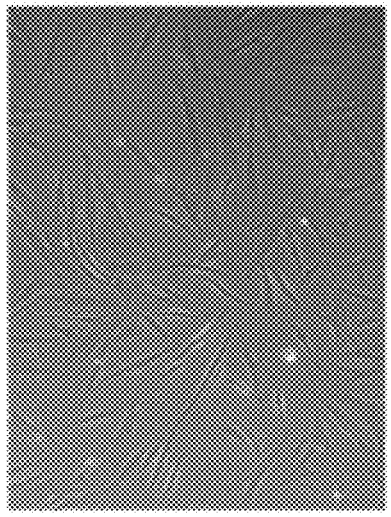
FIGS. 12A, 12B, 12C, and 12D are microscopy images of treated male HFDP cells in concentrations as follows.
Figure 12B:
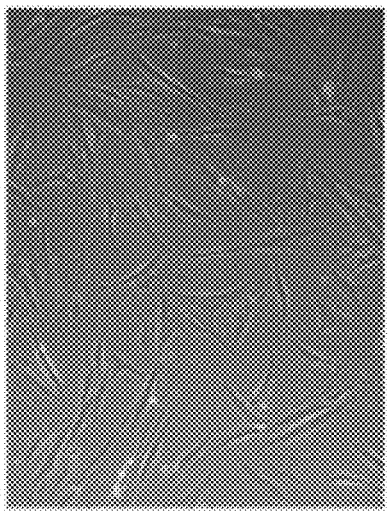
Figure 12C:
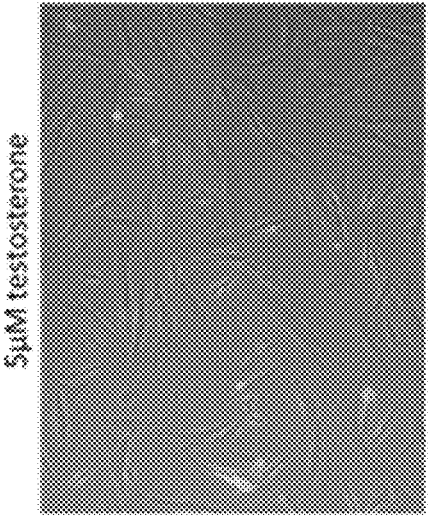
Figure 12D:
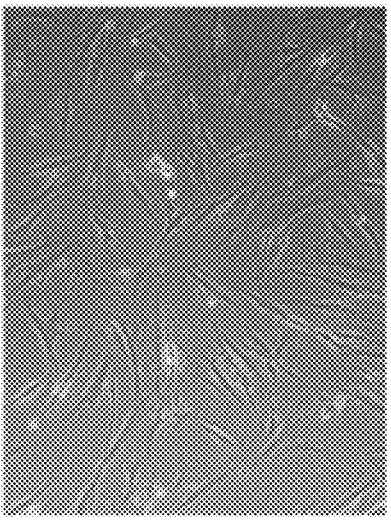

Referring to FIG. 11, it reports results of measuring dihydrotestosterone (DHT) levels in cells treated with the ZM-26 composition. DHT levels were 4.4 fold increased in male HFDP cells treated with 5 μM testosterone. In this study, HFDP cells were previously treated for 8 h with the ZM-26 composition or ZM-26A composition, and then treated with 5 μM of testosterone. The ZM-26 composition in capsule or liquid form does not exert its action through blockage of DHT production.

FIGS. 12A-12D are additional figures from the study described in connection with FIG. 11. These are microscopy images of male HFDP cells treated with the ZM-26 compositions as discussed in connection with FIG. 11.

Figure 13:
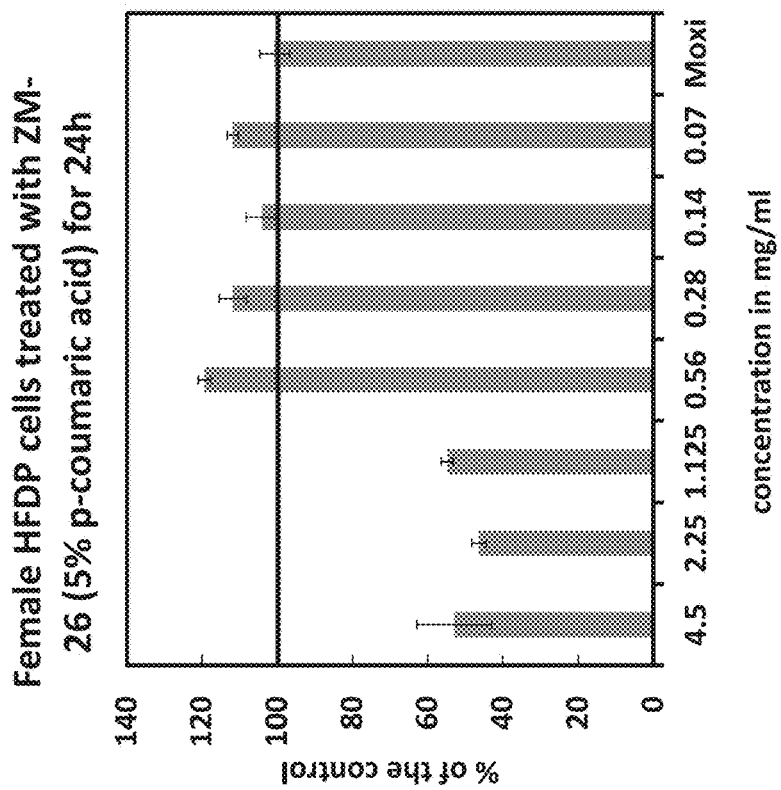
FIG. 13 is a growth curve for female HFDP cells treated with the ZM-26 composition comprising 5% p-coumaric acid for 24 h.

Referring to FIG. 13, it provides results of cell viability in female HFDP cells treated with different concentrations of the ZM-26 composition comprising 5% of p-coumaric acid, based on the volume of the composition total.

Figure 14:
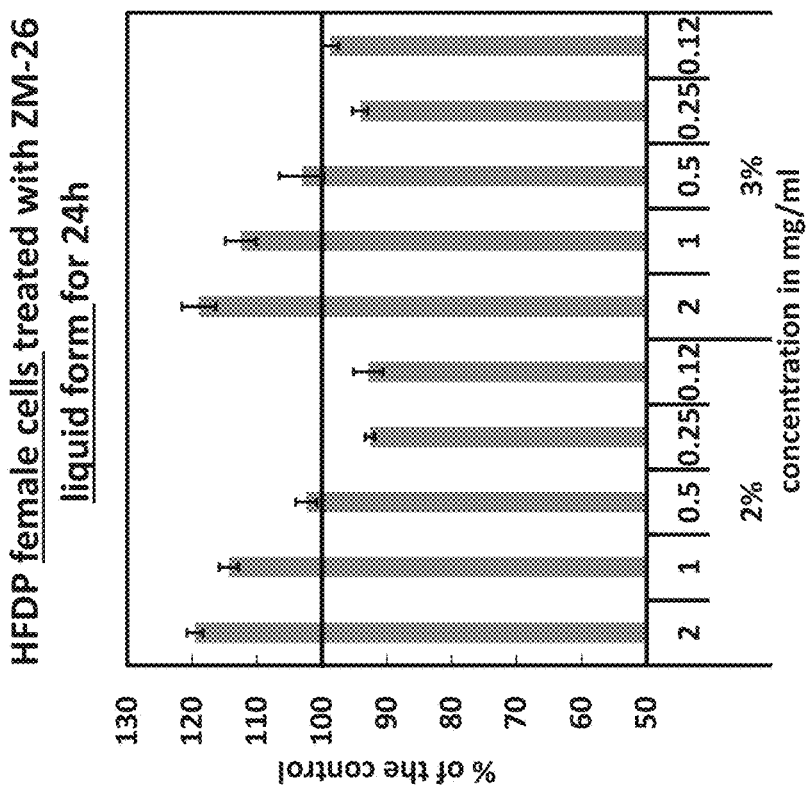
FIG. 14 is a growth curve for female HFDP cells treated with the ZM-26 composition in liquid form comprising either 2% or 3% of p-coumaric acid for 24 h.

Referring to FIG. 14, it reports results of additional studies in HFDP female cells with two different concentrations of p-coumaric acid: 2% and 3%. In this study, the ZM-26 composition was used in liquid form.

Figure 15:
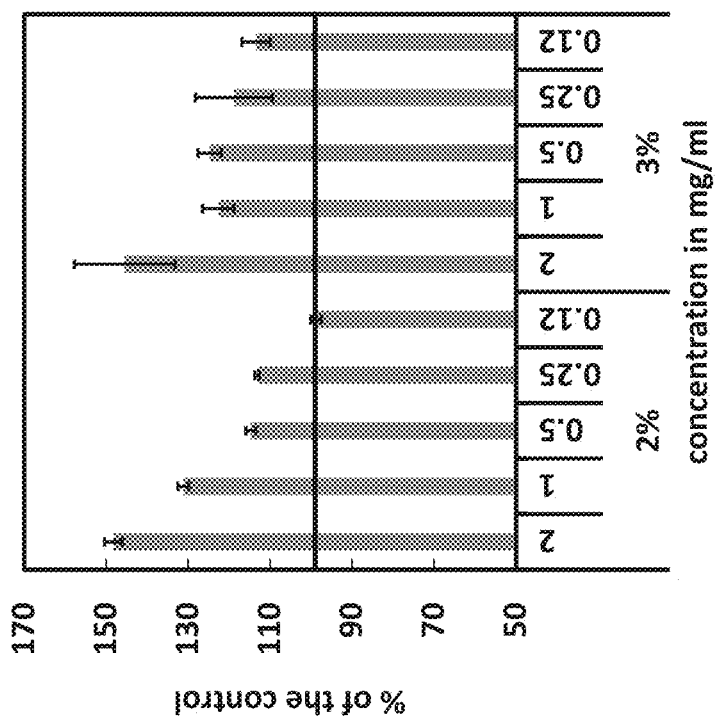
FIG. 15 is a growth curve for female HFDP cells treated with the ZM-26 composition in the encapsulated form and comprising either 2% or 3% of p-coumaric acid for 24 h.

Referring to FIG. 15, it reports results of additional studies in HFDP female cells with two different concentrations of p-coumaric acid: 2% and 3%. In this study, the ZM-26 composition was used in encapsulated form.

Figure 16:
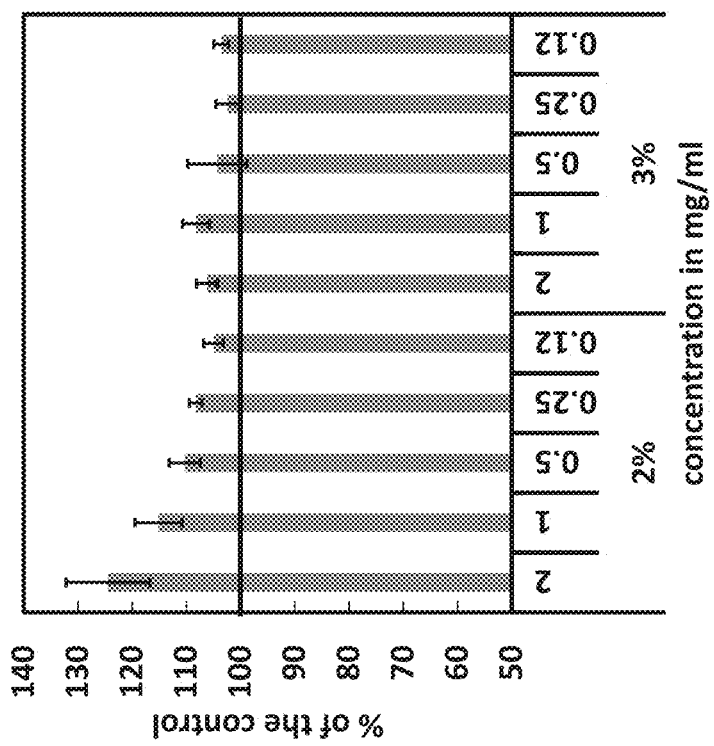
FIG. 16 is a growth curve for male HFDP cells treated with the ZM-26 composition in liquid form and comprising either 2% or 3% of p-coumaric acid for 24 h.

Referring to FIG. 16, it reports results of studies in HFDP male cells with two different concentrations of p-coumaric acid: 2% and 3%. In this study, the ZM-26 composition was used in a liquid form.

Figure 17:
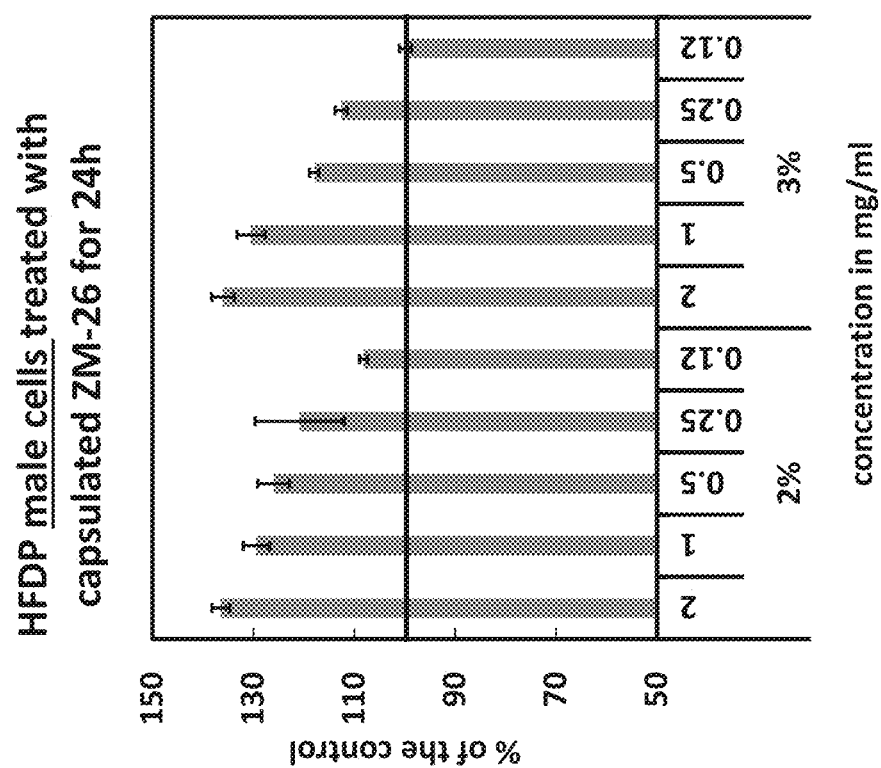
FIG. 17 is a growth curve for male HFDP cells treated with the ZM-26 composition in encapsulated form comprising either 2% or 3% of p-coumaric acid for 24 h.

Referring to FIG. 17, it reports results of studies in HFDP male cells with two different concentrations of p-coumaric acid: 2% and 3%. In this study, the ZM-26 composition was used in encapsulated form.

Referring to FIGS. 18A and 18B, they report a study of TGF-β1 expression in HFDP male cells treated with 2 mg/ml of the ZM-26 composition for 24 hours. As can be seen from a Western blot in FIG. 16B and confirmed by the densitometry analysis in FIG. 16A of the Western blot of FIG. 16B, each of the ZM-26 compositions, either as a capsule or in liquid form, was efficient in suppressing expression of TGF-β1 protein.

Referring to FIGS. 19A and 19B, they report a study of TGF-β1 expression in female HFDP cells treated with 2 mg/ml of the ZM-26 composition for 24 hours. As can be seen from a Western blot in FIG. 17B and as confirmed by the densitometry analysis in FIG. 17A of the Western blot of FIG. 17B, the ZM-26 composition in the capsule form was efficient in suppressing expression of TGF-β1 protein.

Without wishing to be bound by a theory, it is believed that the mechanism of action of the present compositions of this disclosure is based on the synergistic effects of the components acting simultaneously in different pathways, such as stimulating cell proliferation of hair tissue by upregulating cell growth related proteins and by promoting vasodilation in peripheral micro circulation, improving nutrition of the hair follicles, restoring damaged cells from the oxidative stress, and therefore promoting growth of the hair bulb.

Additionally, it was found that the compositions of this disclosure, in contrary to finasteride, are capable to significantly reduce the expression of transforming growth factor-β1 (TGF-β1) in hair follicle dermal papilla cells (HFDPCs) without affecting the DHT production. Thus, the compositions of this disclosure simultaneously act in variety of hair loss related mechanisms aiming at overcoming the multifactorial pattern of most of alopecia disorders found in the human population, including women. Accordingly, the compositions of this disclosure can be used for treating human subjects with multifactorial pattern of alopecia disorders, including women.

Human follicle dermal papilla (HFDP) cells and keratinocytes (HaCaT) were used as models in studies of FIGS. 1-17 by virtue of their relevance to hair growth. HFDP cells are major components of a hair follicle and responsible for the production of essential growth factors. Among the functions of these growth factors is modulation of the follicular epithelium proliferation and acting as a cytokine network controlling follicle development (22). Several studies have shown that a size of the dermal papilla is closely associated with the hair growth cycle, and the dermal papilla cell number increases in the anagen phase (3, 23). Keratinocytes are part of the hair follicle and hair shaft, and produce the major protein of hair, keratin (24). On the basis of its proliferative effect, the compositions of this disclosure were investigated for their hair growth-promoting effect by viability means and at the protein level in both male and female HFDP and HaCaT cells.

The compositions of this disclosure show a remarkable effectiveness in stimulating cell growth in all types of DPCs and HaCaT cells. Western blot analysis revealed two proteins that could be responsible for the observed proliferation effect, one of them is the extracellular signal-regulated kinase 1 and 2 (ERK1/2) which showed a significant increase in its phosphorylated active form upon treatment with the ZM-26 composition.

Studies on hair growth have shown that several signaling proteins, such as Wnt/β-catenin and extracellular signal regulated kinases (ERK), were upregulated in dermal papilla cells after minoxidil treatment and led to the proliferation of dermal papilla cells (25, 26). The ERK pathway has been shown to affect cellular functions including cell proliferation and apoptosis (27, 28). Several activators of hair-growth, such as the vascular endothelial growth factor, placental growth factor, and adenosine, have displayed ERK-mediated hair growth effects (29, 30).

Another protein important in the process of cell growth is the transforming growth factor 1 (TGF-β1) which is a member of the cytokine super-family in mammals and regulates apoptosis in many cell types. TGF-β1 has recently been coined as hair follicle assassin probably by virtue of its central role in inflammation that is associated with hair follicle miniaturization, fibrosis, epithelial cell growth inhibition, and eventual loss (31, 32).

As shown in this disclosure, the compositions of this disclosure lead to a significant suppression of TGF-β1 expression in both male and female DPCs, although the effect in female cells was more moderate. Additionally, TGF-β1 downregulation was also observed in HaCaT cells. Other FDA approved drug for AGA treatment with a similar effect regarding TGF-β1 expression is Finasteride, a type II 5α-reductase inhibitor which has been shown to cure androgenetic alopecia by a reduction of DHT levels in the scalp (33, 34). However, it has been reported that the use of finasteride could cause weaknesses, including transient action and infertility problems due to its interference in the DHT production (35, 36).

Besides, in humans, DHT is essential to induce the production of epidermal growth factor (EGF), keratinocyte growth factor (KGF), and insulin-like growth factors (IGFs), all of which stimulate cellular proliferation (37). Thus, one of the technical benefits provided by the compositions of this disclosure is that the compositions of these disclosure suppress TGF-β1 expression in male and female HFDP cells similar as finasteride. But unlike finasteride, the compositions of this disclosure do not interfere with physiologic production of DHT.

Another issue related to alopecia is oxidative stress. Studies suggest that as a human subject ages, his/her endogenous antioxidant capacities become impaired and cannot keep up with neutralizing naturally-occurring free radicals as well as those that are induced from environmental factors (such as cigarette smoke and UV radiation)(38). Certainly, age-associated dietary deficiencies may contribute to decreased natural antioxidant production since many vital nutrients (e.g., copper, manganese, selenium, and zinc) are needed to produce these enzymes. In fact, one of the symptoms of these nutrient deficiencies is often thinning hair (39). When free radicals are not inhibited by antioxidant molecules within the body, the oxidative damage accumulates, contributing to and causing effects of aging and further impairment of the antioxidant defense system. Evidence from scientific experiments indicates that this happens in hair follicles which can promote hair loss, whether temporary or permanent (40).

Another technical benefit provided by the compositions of this disclosure is that male HFDP cells treated with the compositions of this disclosure overcome the oxidative stress conditions generated by the AAPH compound.

The compositions of this disclosure promote hair growth via stimulation and activation of the transcription factor ERK1/2. They protect hair follicles from the oxidative stress. The compositions of this disclosure suppress the TGF-β1 expression in keratinocytes and HFDP cells without blocking the DHT production. The compositions of this disclosure are more potent in increasing cell proliferation than minoxidil.

Further embodiments of this disclosure include the use of the compositions of this disclosure as non-androgenic multifactorial hair growth-promoting product for treating multifactorial alopecia.

The invention will be now described in more detail by the following non-limiting examples.

Example 1

A formulation was prepared as follows:

50 ml of *Euterpe oleracea* (acai) hydroalcoholic extract was prepared according to the following procedure: 5 grams of *Euterpe oleracea* berry dried extract, concentrated as 5:1, was added to 50 ml of EtOH 90%. The mixture was stirred in an Erlenmeyer flask with a magnetic stirrer at 750 rpm for 2 hours (room temperature). The mixture was then evaporated in a rotavapor to provide a concentrate with a final volume of 5 ml of a thick viscous liquid.

3 ml of *Olea europaea* hydroalcoholic extract 1:3 was prepared as follows. Hydroalcoholic (50% ethanol and 50% distilled water v/v) extract of the leaves was prepared using a percolation method. The yield was about 30-35%. This extract was then evaporated in a rotavapor and concentrated to a final volume of 0.3 ml of a viscous liquid.

3 ml of *Coffea arabica* 1:3 tincture (green coffee beans) was prepared as follows. The *Coffea arabica* tincture was concentrated by evaporation in a rotavapor to a final volume of 0.3 ml of a viscous liquid.

1 ml of *Tabebuia impetiginosa* tincture—was concentrated by evaporation in a rotavapor to a final volume of 0.1 ml of a viscous liquid.

Zinc oxide was added in the amount of 5 mg. Vitamin D3 (cholecalciferol) was added in the amount of 10 mg, and p-coumaric acid was added in the amount of 10 mg.

The composition comprised 5.7 ml of a solution to which 25 mg of powder was added. The mixture was the basis to be added to a gel at a concentration of 3%.

The *Olea europaea* leaf extract was tested for an amount of oleuropein by HPLC. The *Euterpe oleracea* Acai berry extract was tested for an amount of cyanidin 3-glucoside and for an amount of cyanidin 3-rutinoside by HPLC.

Example 2. Materials and Methods for Studies in Connection with FIGS. 1-17

Cell Culture and Treatment

Adherent human cell lines were cultured according to standard mammalian tissue culture protocols and sterile technique. Human follicle derma papilla cells were cultured in human follicle dermal papilla cell growth medium, ready to use, low-serum. Keratinocyte cells (HaCaT) were cultured in high glucose Dulbecco's Modified Eagle Medium with 10% serum. Normal human epithelial cells such as HFF and BJ were culture in BIOAMF-2 complete medium (Biological industries). All media was supplemented with streptomycin (100 mg/ml), penicillin (100 U/ml) and Nystatin (12.5 U/ml). Cells were incubated in 5% $CO_2$ at 37° C. All tissue culture were maintained in 25 $cm^2$ Nunc™ cell culture treated EasYFlask™ (Thermofisher scientific) and all the media and supplements were obtained from Biological Industries. Treatment were performed by plating cells in a Nunc™ 96 micro well delta surface plates (Thermofisher scientific) in a starting confluence of $0.5 \times 10^4$ cells/well. After 24 h of incubation the cells were treated with the ZM-26 composition.

MTT Assay

Viability of the cells following treatment was determined using a commercially available MTT assay kit (ABCAM, ab146345) and performed according to manufacturer's instructions. Briefly, cells were seeded in a 96-well plates at a density of $0.5 \times 10^4$ cells/well (n=4). After overnight plating, cells were exposed to varying concentrations of ZM-26 composition (9-0.07 mg/ml). Then, plates were incubated in a humidified atmosphere containing 5% $CO_2$ in air at 37° C. for 24 hours. According to the MTT standard protocol, after 24 and 48 h treatment, the media was removed and all cells were incubated with serum-free media containing 0.5 mg/ml MTT for 4 hours at the incubator. The MTT purple crystals formed by the viable cells were diluted using isopropanol containing 0.04 mol/L HCL. The quantification was determined by measuring the optical density at 570 nm in an enzyme-linked immunosorbent assay (Spark, Tecan) reader. Data was presented as proportional viability (%) by comparing the treated group with the untreated cells, the viability of which is assumed to be 100%.

Protein Extraction and Western Blot Analysis

Whole cell lysate was prepared by washing cells pellets with 1× Phosphate buffer saline (Biological Industries), resuspending it in ice cold T lysis buffer [50 mM Tris-Cl (pH 7.5), 150 mM NaCl, 1 mM EDTA, 1% Triton X and 1× Halt™ protease and phosphatase inhibitor cocktail] and incubating for 30 minutes in ice. The lysate was followed by centrifugation at 13,800 g for 10 min at 4° C. to clear the cellular debris. Total protein was quantified using the Bradford protein assay kit (Biorad, Hercules, Calif.). Equal amount of protein was resolved on precast Bolt™ 4-12% Bis-Tris Plus polyacrylamide gel (Invitrogen), electro-transferred to precast nitrocellulose stacks using iBlot®2 system (Invitrogen) and western blot analysis was performed using the antibodies described above. Immuno-detection was performed by blocking the membranes for 1 h in TNT buffer [10 mM Tris-Cl (pH 7.5), 150 mM NaCl, 0.05% Tween-20] containing 5% powdered non-fat milk followed by addition of the primary antibody (as indicated) in TNT for 2 h at room temperature. Specifically bound primary antibodies were detected with peroxidase-coupled secondary antibodies and developed by enhanced chemiluminescence (biological industries) according to manufacturer's instructions and quantitated using ImageQaunt LAS 4000 mini, General Electric). All experiments were performed at least three-five times using independent biological replicates.

Immunoblot Analysis

Immunoblot analysis was performed using antibodies against ERK1 phospho T202+ERK2 phospho T186 (1:1000 dilution; ab201015, Abcam), GAPDH (1:6000 dilution; ab128915, Abcam), beta Actin (1:1000 dilution; 101173, Abcam), TGF-beta (1:500 dilution; ab179695, abcam), Species-specific HRP-labeled secondary antibodies were then added. The blots were visualized using enhanced chemiluminescence (biological industries) and quantitated using ImageQaunt LAS 4000 mini, General Electric).

ELISA for DHT Detection

Dihydrotestosterone (DHT) detection was performed using the Aviva Systems Biology dihydrotestosterone ELISA kit (OKEH02531). The technique is based on a competitive binding enzyme immunoassay. 96 well plate has been pre-coated with an antibiotinylated dihydrotestosterone antibody. 50 µl of male HFDP cells control and treated samples were added to the wells along with 50 µl of 1× dihydrotestosterone-Biotin complex. After incubation at 37° C. for 60 min wells were washed 3 times with 1× Wash buffer and was added to each well 100 µl of Avidin-HRP conjugate solution. Another step of incubation at 37° C. for 45 min and washing with 1× wash buffer was performed. 90 µl of TMB subtract was added and to each well followed by incubation in dark, 37° C. for 15-30 minutes. Finally, 50 µl of a stop solution was added and the quantification was determined by measuring the optical density at 450 nm in an enzyme-linked immunosorbent assay (Spark, Tecan) reader.

Oxidative Stress Assay

HFDP cells were plated in a Nunc™ 96 micro well delta surface plates (Thermofisher scientific) in a starting confluence of $0.5 \times 10^4$ cells/well. After 24 h of incubation the cells were cotreated with different concentration of the ZM-26 composition and 10 mM of AAPH or only with AAPH (control cells) as elucidate in the experiments displayed in the results section. The concentration of AAPH selected to perform this assay was determined by the minimal concentration able to reduce cell viability to 30% (EC30). After another turn of 24 h incubation in 37° C. 5% cell viability was determined using a commercially available MTT assay kit (ABCAM, ab146345) and performed according to manufacturer's instructions.

LIST OF CITED REFERENCES

1. Stenn, K. S. and Paus, R. (2001) Controls of hair follicle cycling. *Physiol. Rev.,* 81, 449-494.
2. Ozeki, M. and Tabata, Y. (2003) In vivo promoted growth of mice hair follicles by the controlled release of growth factors. *Biomaterials,* 24, 2387-94.
3. Rho, S.-S., Park, S.-J., Hwang, S.-L., Lee, M.-H., Kim, C. D., Lee, I.-H., Chang, S.-Y. and Rang, M.-J. (2005) The hair growth promoting effect of Asiasari radix extract and its molecular regulation. *J. Dermatol. Sci.,* 38, 89-97.
4. Kamimura, J., Lee, D., Baden, H. P., Brissette, J. and Dotto, G. P. (1997) Primary mouse keratinocyte cultures contain hair follicle progenitor cells with multiple differentiation potential. *J. Invest. Dermatol.,* 109, 534-40.
5. McElwee, K. J. and Sinclair, R. (2008) Hair physiology and its disorders. *Drug Discov. Today Dis. Mech.,* 5, 163-171.
6. Venning, V. A. and Dawber, R. P. (1988) Patterned androgenic alopecia in women. *J. Am. Acad. Dermatol.,* 18, 1073-7.
7. HAMILTON, J. B. (1951) Patterned loss of hair in man; types and incidence. *Ann. N. Y. Acad. Sci.,* 53, 708-28.
8. Dinh, Q. Q. and Sinclair, R. (2007) Female pattern hair loss: current treatment concepts. *Clin. Interv. Aging,* 2, 189-99.
9. Messenger, A. G. and Rundegren, J. (2004) Minoxidil: mechanisms of action on hair growth. *Br. J. Dermatol.,* 150, 186-94.
10. Gupta, A. K. and Charrette, A. Topical Minoxidil: Systematic Review and Meta-Analysis of Its Efficacy in Androgenetic Alopecia. *Skinmed,* 13, 185-9.
11. Aktas, H., Alan, S., Türkoglu, E. B. and Sevik, O. (2016) Could Topical Minoxidil Cause Non-Arteritic Anterior Ischemic Optic Neuropathy? *J. Clin. Diagn. Res.,* 10, WD01-2.
12. Mysore, V. (2012) Finasteride and sexual side effects. *Indian Dermatol. Online J.,* 3, 62.
13. Kiguradze, T., Temps, W. H., Yarnold, P. R., Cashy, J., Brannigan, R. E., Nardone, B., Micali, G., West, D. P. and Belknap, S. M. (2017) Persistent erectile dysfunction in men exposed to the 5α-reductase inhibitors, finasteride, or dutasteride. *PeerJ,* 5, e3020.
14. Sawaya, M. E. and Shapiro, J. (2000) Androgenetic alopecia. New approved and unapproved treatments. *Dermatol. Clin.,* 18, 47-61, viii.
15. Rose, P. (2015) Hair restoration surgery: challenges and solutions. *Clin. Cosmet. Investig. Dermatol.,* 10.2147/CCID.S53980.
16. Boisvert, W. A., Yu, M., Choi, Y., Jeong, G. H., Zhang, Y.-L., Cho, S., Choi, C., Lee, S. and Lee, B.-H. (2017) Hair growth-promoting effect of *Geranium sibiricum* extract in human dermal papilla cells and C57BL/6 mice. *BMC Complement. Altern. Med.,* 17, 109.
17. Oh, J. Y., Park, M. A. and Kim, Y. C. (2014) Peppermint Oil Promotes Hair Growth without Toxic Signs. *Toxicol. Res.,* 30, 297-304.
18. Patel, S., Sharma, V., Chauhan, N. S., Thakur, M. and Dixit, V. K. (2015) Hair Growth: Focus on Herbal Therapeutic Agent. *Curr. Drug Discov. Technol.,* 12, 21-42.
19. Kumar, N., Rungseevijitprapa, W., Narkkhong, N.-A., Suttajit, M. and Chaiyasut, C. (2012) 5α-reductase inhibition and hair growth promotion of some Thai plants traditionally used for hair treatment. *J. Ethnopharmacol.,* 139, 765-71.
20. Jadhav, V. M., Thorat, R. M., Kadam, V. J. and Gholve, S. B. (2009) Kesharaja: Hair vitalizing herbs. *Int. J. PharmTech Res.,* 1, 454-467.
21. Gupta, M. and Mysore, V. Classifications of Patterned Hair Loss: A Review. *J. Cutan. Aesthet. Surg.,* 9, 3-12.
22. Rushan, X., Fei, H., Zhirong, M. and Yu-zhang, W. (2007) Identification of proteins involved in aggregation of human dermal papilla cells by proteomics. *J. Dermatol. Sci.,* 48, 189-197.
23. Datta, K., Singh, A. T., Mukherjee, A., Bhat, B., Ramesh, B. and Burman, A. C. (2009) Eclipta alba extract with potential for hair growth promoting activity. *J. Ethnopharmacol.,* 124, 450-6.
24. Klima, J., Smetana, K., Motlik, J., Plzáková, Z., Liu, F.-T., Stork, J., Kaltner, H., Chovanec, M., Dvoránková, B., André, S., et al. (2005) Comparative phenotypic characterization of keratinocytes originating from hair follicles. *J. Mol. Histol.,* 36, 89-96.
25. Kwack, M. H., Kang, B. M., Kim, M. K., Kim, J. C. and Sung, Y. K. (2011) Minoxidil activates β-catenin pathway in human dermal papilla cells: a possible explanation for its anagen prolongation effect. *J. Dermatol. Sci.,* 62, 154-9.
26. Dastan, M., Najafzadeh, N., Abedelahi, A., Sarvi, M. and Niapour, A. (2016) Human platelet lysate versus minoxidil stimulates hair growth by activating anagen promoting signaling pathways. *Biomed. Pharmacother.,* 84, 979-986.
27. Molavi, O., Narimani, F., Asiaee, F., Sharifi, S., Tarhriz, V., Shayanfar, A., Hejazi, M. and Lai, R. (2017) Silibinin sensitizes chemo-resistant breast cancer cells to chemotherapy. *Pharm. Biol.,* 55, 729-739.
28. Gunda, V., Sarosiek, K. A., Brauner, E., Kim, Y. S., Amin, S., Zhou, Z., Letai, A. and Parangi, S. (2017) Inhibition of MAPKinase pathway sensitizes thyroid cancer cells to ABT-737 induced apoptosis. *Cancer Lett.,* 395, 1-10.
29. Hwang, K.-A., Hwang, Y.-L., Lee, M.-H., Kim, N.-R., Roh, S.-S., Lee, Y., Kim, C. D., Lee, J.-H. and Choi, K.-C. (2012) Adenosine stimulates growth of dermal papilla and lengthens the anagen phase by increasing the cysteine level via fibroblast growth factors 2 and 7 in an organ culture of mouse vibrissae hair follicles. *Int. J. Mol. Med.,* 29, 195-201.
30. Li, W., Man, X.-Y., Li, C.-M., Chen, J.-Q., Zhou, J., Cai, S.-Q., Lu, Z.-F. and Zheng, M. (2012) VEGF induces proliferation of human hair follicle dermal papilla cells through VEGFR-2-mediated activation of ERK. *Exp. Cell Res.,* 318, 1633-40.
31. Inui, S., Fukuzato, Y., Nakajima, T., Yoshikawa, K. and Itami, S. (2002) Androgen-inducible TGF-beta1 from balding dermal papilla cells inhibits epithelial cell growth: a clue to understand paradoxical effects of androgen on human hair growth. *FASEB J.,* 16, 1967-9.
32. Li, A. G., Lu, S.-L., Han, G., Hoot, K. E. and Wang, X.-J. (2006) Role of TGFbeta in skin inflammation and carcinogenesis. *Mol. Carcinog.,* 45, 389-96.
33. Kaufman, K. D., Olsen, E. A., Whiting, D., Savin, R., DeVillez, R., Bergfeld, W., Price, V. H., Van Neste, D., Roberts, J. L., Hordinsky, M., et al. (1998) Finasteride in the treatment of men with androgenetic alopecia. Finasteride Male Pattern Hair Loss Study Group. *J. Am. Acad. Dermatol.,* 39, 578-89.
34. Dallob, A. L., Sadick, N. S., Unger, W., Lipert, S., Geissler, L. A., Gregoire, S. L., Nguyen, H. H., Moore, E. C. and Tanaka, W. K. (1994) The effect of finasteride, a 5 alpha-reductase inhibitor, on scalp skin testosterone and dihydrotestosterone concentrations in patients with male pattern baldness. *J. Clin. Endocrinol. Metab.,* 79, 703-6.
35. Rossi, A., Anzalone, A., Fortuna, M. C., Caro, G., Garelli, V., Pranteda, G. and Carlesimo, M. (2016) Multi-therapies in androgenetic alopecia: review and clinical experiences. *Dermatol. Ther.,* 29, 424-432.
36. Tu, H. Y. V. and Zini, A. (2011) Finasteride-induced secondary infertility associated with sperm DNA damage. *Fertil. Steril.,* 95, 2125.e13-4.
37. Dicker A. P., Merrick G., Gomella L., Valicenti R. K., W. F. (2005) Basic and advanced techniques in prostate brachytherapy.
38. Rahman, T., Hosen, I., Islam, M. M. T. and Shekhar, H. U. (2012) Oxidative stress and human health. *Adv. Biosci. Biotechnol.,* 3, 997-1019.

39. Guo, E. L. and Katta, R. (2017) Diet and hair loss: effects of nutrient deficiency and supplement use. *Dermatol. Pract. Concept.*, 7, 1-10.
40. Trüeb, R. M. (2009) Oxidative stress in ageing of hair. *Int. J. Trichology*, 1, 6-14.

What is claimed is:

1. A composition consisting essentially of:
   1) the following extracts:
      a) an *Euterpe oleracea* extract comprising cyanidin 3-glycoside and/or cyanidin 3-rutinoside,
      b) an *Olea europaea* extract comprising oleuropein,
      c) a *Coffea arabica* green beans extract, and
      d) a *Tabebuia* impetiginosa extract;
   2) a micronutrient comprising zinc;
   3) vitamin D3;
   4) magnesium citrate; and
   5) calcium d-pantothenate;
   wherein per each 100 to 150 mg of the *Euterpe oleracea* extract in the composition, the composition consists essentially of 55 to 105 mg of the *Tabebuia impetiginosa* extract, 55 to 105 mg of the *Olea europaea* dried leaves extract comprising oleuropein; 50 to 100 mg of the *Coffea arabica* green beans extract, and 200 to 2000 International Units (IUs) of Vitamin D3; and
   wherein the composition stimulates hair regrowth and hair micro vascularization in male and female subjects with alopecia.

2. The composition of claim 1, wherein the composition further consists essentially of p-coumaric acid.

3. The composition of claim 2, wherein the *Euterpe oleracea* extract is a hydroalcoholic berry extract comprising cyanidin 3-glucoside and cyanidin 3-rutinoside; the *Tabebuia impetiginosa* extract is a bark tincture; the *Olea europaea* extract is a hydroalcoholic leaf extract; and the micronutrient comprising zinc is zinc oxide.

4. The composition of claim 1, wherein the *Euterpe oleracea* extract is a berry extract and the *Tabebuia impetiginosa* extract is a bark extract.

5. The composition of claim 1, wherein the extracts are hydroalcoholic extracts and/or wherein the *Euterpe oleracea* extract is a 2:1 to 10:1 concentrate.

6. The composition of claim 1, wherein the composition further has one or more of the following features: the *Euterpe oleracea* extract is obtained from Acai berries; the *Coffea arabica* extract is obtained from *Coffea arabica* unroasted green beans; and/or the micronutrient comprising zinc comprises zinc oxide or zinc picolinate.

7. The composition of claim 1, wherein the zinc source in the micronutrient comprising zinc is zinc picolinate.

8. The composition of claim 1, wherein per each 100 to 150 mg of the *Euterpe oleracea* extract in the composition; an amount of calcium d-pantothenate is in the range from 0.1 to 10 mg; an amount of magnesium citrate is in the range from 0.1 to 100 mg; and an amount of the micronutrient comprising zinc is 5 to 20 mg of zinc picolinate.

9. The composition of claim 1, wherein the composition further consists essentially of an inert ingredient.

10. The composition of claim 1, wherein the composition further consists essentially of ethanol, starch, modified starch, microcrystalline cellulose, or any combination thereof.

11. The composition of claim 1, wherein the composition is spray-dried and encapsulated within at least one carrier.

12. The composition of claim 1, wherein the composition is formulated for oral administration as a food product, beverage, juice, chewables, syrup, powder, granules, tea bag, tablet, pill, powder, capsules, softgel capsules, liquid or drops; or
   wherein the composition is formulated for a topical application as a lotion, gel, cream, ointment, hair shampoo, hair conditioner, hair spray, hair foam, soap, patch, powder, tissue or a sprayable powder.

13. A dietary supplement or topical formulation comprising the composition of claim 1.

14. The composition of claim 1 wherein the *Euterpe oleracea* extract is a *Euterpe oleracea* concentrate, and wherein the composition further consists essentially of L-arginine.

15. The composition of claim 14 which consisting essentially of:
   *Euterpe oleracea* as a freeze-dried concentrate 1:4—100 mg to 300 mg;
   *Tabebuia impetiginosa* extract—100 mg to 200 mg;
   Oleuropein from *Olea europaea* dried leaves—50 mg to 150 mg; Vitamin D3 (Cholecalciferol)—300 UI to 500 UI;
   L-arginine—150 mg to 200 mg;
   Calcium d-pantothenate—0.5 mg to 5 mg; and
   Magnesium citrate—200 to 400 mg.

16. A non-medicinal method for rejuvenating hair in a human subject, the method comprising administering to the human subject the composition of claim 1.

17. The method of claim 16, wherein the human subject is administered the composition as a dietary supplement and/or as a topical formulation.

* * * * *